United States Patent
Quan et al.

(10) Patent No.: US 6,902,903 B1
(45) Date of Patent: Jun. 7, 2005

(54) HELICOBACTER PYLORI DIAGNOSTICS

(75) Inventors: Stella Quan, Emeryville, CA (US); Pablo Valenzuela, Berkeley, CA (US); Alan Polito, Emeryville, CA (US)

(73) Assignee: Chiron Corporation, Emeryville, CA (US)

( * ) Notice: Subject to any disclaimer, the term of this patent is extended or adjusted under 35 U.S.C. 154(b) by 418 days.

(21) Appl. No.: 08/993,010

(22) Filed: Dec. 18, 1997

Related U.S. Application Data
(60) Provisional application No. 60/033,707, filed on Dec. 19, 1996.

(51) Int. Cl.$^7$ ............................................. G01N 33/554
(52) U.S. Cl. ............................ 435/7.32; 435/34; 435/5; 435/6; 435/94; 435/7.2; 435/7.92; 435/7.93; 435/252.1; 435/7.4; 436/172; 436/518; 436/530; 536/24.3; 536/24.32; 536/23.1; 536/22.1
(58) Field of Search .................... 435/7.32, 7.92, 435/34, 7.2, 252.1, 7.9, 7.42, 7.4, 7.93, 5, 6, 94, 32; 536/23.1, 22.1, 24.3, 24.23; 436/172, 518, 530

(56) References Cited

U.S. PATENT DOCUMENTS

| | | | | |
|---|---|---|---|---|
| 5,262,156 A | * | 11/1993 | Alemohammad | 435/7.32 |
| 5,403,924 A | * | 4/1995 | Cover et al. | 536/23.1 |
| 5,420,014 A | * | 5/1995 | Cripps et al. | 435/7.32 |
| 5,567,594 A | * | 10/1996 | Calenoff | 435/7.32 |
| 5,610,060 A | * | 3/1997 | Ward et al. | 435/252.1 |
| 5,733,740 A | * | 3/1998 | Cover et al. | 435/7.32 |
| 5,814,455 A | * | 9/1998 | Pronovost et al. | 435/7.1 |
| 5,846,751 A | * | 12/1998 | Pronovost et al. | 435/7.32 |
| 5,859,219 A | * | 1/1999 | Cover et al. | 536/22.1 |

FOREIGN PATENT DOCUMENTS

| | | | |
|---|---|---|---|
| WO | 90/03575 | * | 5/1990 |
| WO | 93/16723 | * | 2/1993 |

OTHER PUBLICATIONS

Lage, AP et al, Gut, vol. 37 (Suppl. 1), pA69, abstract # 273, 1995.*
Atherton, J.C. et al, J. Biolog. Chem., vol. 270 No. 30, Jul. 28, pp 17771–17777, 1995.*
Apel et al, Zbl.Bakt. Hyg., vol. A268, pp. 271–276, 1988.*
Landini et al, Microbiologica, vol. 12, pp. 181–188, 1989.*
Crabtree, J.E. et al. J. Clin. Pathol., vol. 48, pp. 41–45, 1995.*
vonWulffen et al, J.Clin. Pathol. vol. 41, pp. 653–659, 1988.*
Cover, TL et al. Infection and Immunity, Mar. 1990, vol. 58(3), pp. 603–610.*
Vijayakumari,S et al. Cytobios, vol. 82, pp. 251–260, 1995.*
Tummuru, M,et al, Infection and Immunity, vol. 61(5), May 1993, pp. 1799–1809.*

(Continued)

*Primary Examiner*—Lynette R. F. Smith
*Assistant Examiner*—Ginny Allen Portner
(74) *Attorney, Agent, or Firm*—Dahna S. Pasternak; Rebecca M. Hale; Alisa A. Harbin

(57) ABSTRACT

Novel methods, membrane supports and immunodiagnostic test kits for diagnosing *Helicobacter pylori* infection, are disclosed. The methods can also be used to monitor the progress of treatment of an infection. The methods, supports and kits employ both type-common and type-specific *H. pylori* antigens and can conveniently be performed in a single-step assay format. The methods provide for highly accurate results and discriminate between *H. pylori* Type I and *H. pylori* Type II infection so that an accurate diagnosis can be accomplished.

17 Claims, 5 Drawing Sheets

OTHER PUBLICATIONS

Figura, N. European Journal of Gastroenterology and Hepatology, 1995, vol. 7(4), pp. 296–302.*

Xiang, Z et al. Infection and Immunity, vol. 63(1), Jan. 1995, pp. 94–98.*

Karnes, WE, Jr. et al. Gastroenterology, 1991, vol. 161, pp. 167–174.*

Marshall, BJ, vol. 7, No. 6, May, 1995, Shokaki Naishikyo, Indoscopia Digestiva, pp. 793–799.*

Rhee, Kwang Ho et al, 1992, Taehan Misaengmul Hakhoechi, vol. 27(2), pp. 143–154 (eng. transl).*

Schmitt et al, Molecular Microbiology, Apr. 1994, vol. 12(2), pp. 307–319.*

Sharma, S et al. Infection and Immunity, May 1995, vol. 63(5), pp. 1681–1687.*

Ng, TM et al, J. Gastroenterol. and Hepatol., vol. 10, Sep. 1995, issue S3, p. A81, abs.no.E65.*

Crabtree, JE et al., European J. Gastroenterol. Hepatol., 1994, vol. 6(suppl. 1), pp. 533–538.*

Fackelmann, K. Science News, vol. 147(11), p. 165(1), Mar. 18, 1995.*

Atherton, J.C. et al, Gut, vol. 37(suppl. 1), p. A69, Abstract 275, 1995.*

Atherton, J.C. et al, J. Biological Chemistry, vol. 270(30), pp. 17771–17777, 1995.*

Atherton, J.C. et al, Gastroenterology, vol. 108(4 suppl), p. A774, 1995.*

Atherton, J.C. et al, Am. J Gastroenterol. vol. 89(8), Aug. 1994, p. 1291, abstract 26.*

Owen, R.J. et al, FEMS Microbiology Letters, vol. 79, pp. 199–204, 1991.*

Garner, J.A. et al, J. Infectious Dis., 1995, vol. 172, pp. 290–293.*

Pretolani, S et al, Aug 1994, abstract 471, Am. J. Gastroenterol., vol. 89(8).*

Blaser, M.J., Molecular Medicine, vol. 31(12), 1994, pp. 1334–1339.*

Leunk, R.D et al, J. Clinical Microbiology, Jun. 1990, vol. 28(6), pp. 1181–1184.*

Xiang,Z et al, European Journal of Clinical Microbiology and Infectious Disease, Oct. 1993, vol. 12(10), pp. 739–745 (abstract only), Oct. 1993.*

Figura, N, European Journal of Gastroenterology and Hepatology, vol. 7(4), pp. 296–302, 1995.*

Xiang, Z et al, Infection Immunity, vol. 63(1), pp. 94–98, Jan. 1995.*

Crabtree, J.E et al, Digestive Diseases and Science, vol. 36(9), pp. 1266–1273, Sep. 1991.*

* cited by examiner

```
      1                                              10
      M   A   T   K   A   V   C   V   L   K   G   D   G   P   V   Q   G   I   I
CC   ATG GCT ACA AAG GCT GTT TGT GTT TTG AAG GGT GAC GGC CCA GTT CAA GGT ATT ATT
 20                                      30
  N   F   E   Q   K   E   S   N   G   P   V   K   V   W   G   S   I   K   G   L
 AAC TTC GAG CAG AAG GAA AGT AAT GGA CCA GTG AAG GTG TGG GGA AGC ATT AAA GGA CTG
 40                              50
  T   E   G   L   H   G   F   H   V   H   E   F   G   D   N   T   A   G   C   T
 ACT GAA GGC CTG CAT GGA TTC CAT GTT CAT GAG TTT GGA GAT AAT ACA GCA GGC TGT ACC
 60                                              70
  S   A   G   P   H   F   N   P   L   S   R   K   H   G   G   P   K   D   E   E
 AGT GCA GGT CCT CAC TTT AAT CCT CTA TCC AGA AAA CAC GGT GGG CCA AAG GAT GAA GAG
 80                                              90
  R   H   V   G   D   L   G   N   V   T   A   D   K   D   G   V   A   D   V   S
 AGG CAT GTT GGA GAC TTG GGC AAT GTG ACT GCT GAC AAA GAT GGT GTG GCC GAT GTG TCT
100                                              110
  I   E   D   S   V   I   S   L   S   G   D   H   C   I   I   G   R   T   L   V
 ATT GAA GAT TCT GTG ATC TCA CTC TCA GGA GAC CAT TGC ATC ATT GGC CGC ACA CTG GTG
120                                              130
  V   H   E   K   A   D   D   L   G   K   G   G   N   E   E   S   T   K   T   G
 GTC CAT GAA AAA GCA GAT GAC TTG GGC AAA GGT GGA AAT GAA GAA AGT ACA AAG ACA GGA
140                                              150
  N   A   G   S   R   L   A   C   G   V   I   G   I   A   Q   N   L   G   I   L
 AAC GCT GGA AGT CGT TTG GCT TGT GGT GTA ATT GGG ATC GCC CAG AAT TTG GGA ATT CTC
160                                              170
  G   T   L   D   L   W   Q   S   A   G   L   N   I   I   A   P   P   E   G   G
 GGC ACA CTG GAT TTG TGG CAA AGC GCC GGG TTA AAC ATT ATC GCT CCT CCA GAA GGT GGC
180                                              190
  Y   K   D   K   P   N   N   T   P   S   Q   S   G   A   K   N   D   K   N   E
 TAT AAG GAT AAA CCC AAT AAT ACC CCT TCT CAA AGT GGT GCT AAA AAC GAC AAA AAT GAA
200                                              210
  S   A   K   N   D   K   Q   E   S   S   Q   N   N   S   N   T   Q   V   I   N
 AGC GCT AAA AAC GAC AAA CAA GAG AGC AGT CAA AAT AAT AGT AAC ACT CAG GTC ATT AAC
220                                              230
  P   P   N   S   A   Q   K   T   E   V   Q   P   T   Q   V   I   D   G   P   F
 CCA CCC AAT AGT GCG CAA AAA ACA GAA GTT CAA CCC ACG CAA GTC ATT GAT GGG CCT TTT
240                                              250
  A   G   G   K   D   T   V   V   N   I   N   R   I   N   T   N   A   D   G   T
 GCG GGC GGC AAA GAC ACG GTT GTC AAT ATC AAC CGC ATC AAC ACT AAC GCT GAT GGC ACG
260                                              270
  I   R   V   G   G   F   K   A   S   L   T   T   N   A   A   H   L   H   I   G
 ATT AGA GTG GGA GGG TTT AAA GCT TCT CTT ACC ACC AAT GCG GCT CAT TTG CAT ATC GGC
280                                              290
  K   G   G   V   N   L   S   N   Q   A   S   G   R   S   L   I   V   E   N   L
 AAA GGC GGT GTC AAT CTG TCC AAT CAA GCG AGC GGG CGC TCT CTT ATA GTG GAA AAT CTA
300                                              310
  T   G   N   I   T   V   D   G   P   L   R   V   N   N   Q   V   G   G   Y   A
 ACT GGG AAT ATC ACC GTT GAT GGG CCT TTA AGA GTG AAT AAT CAA GTG GGT GGC TAT GCT
320                                              330
  L   A   G   S   S   A   N   F   E   F   K   A   G   T   D   T   K   N   G   T
 TTG GCA GGA TCA AGC GCG AAT TTT GAG TTT AAG GCT GGT ACG GAT ACC AAA AAC GGC ACA
340                                              350
  A   T   F   N   N   D   I   S   L   G   R   F   V   N   L   K   V   D   A   H
 GCC ACT TTT AAT AAC GAT ATT AGT CTG GGA AGA TTT GTG AAT TTA AAG GTG GAT GCT CAT
```

FIG. 3A

```
360                            370
 T   A   N   F   K   G   I   D   T   G   N   G   G   F   N   T   L   D   F   S
ACA GCT AAT TTT AAA GGT ATT GAT ACG GGT AAT GGT GGT TTC AAC ACC TTA GAT TTT AGT
380                            390
 G   V   T   D   K   V   N   I   N   K   L   I   T   A   S   T   N   V   A   V
GGC GTT ACA GAC AAA GTC AAT ATC AAC AAG CTC ATT ACG GCT TCC ACT AAT GTG GCC GTT
400                            410
 K   N   F   N   I   N   E   L   I   V   K   T   N   G   I   S   V   G   E   Y
AAA AAC TTC AAC ATT AAT GAA TTG ATT GTT AAA ACC AAT GGG ATA AGT GTG GGG GAA TAT
420                            430
 T   H   F   S   E   D   I   G   S   Q   S   R   I   N   T   V   R   L   E   T
ACT CAT TTT AGC GAA GAT ATA GGC AGT CAA TCG CGC ATC AAT ACC GTG CGT TTG GAA ACT
440                            450
 G   T   R   S   L   F   S   G   G   V   K   F   K   G   G   E   K   L   V   I
GGC ACT AGG TCA CTT TTC TCT GGG GGT GTT AAA TTT AAA GGT GGC GAA AAA TTG GTT ATA
460                            470
 D   E   F   Y   Y   S   P   W   N   Y   F   D   A   R   N   I   K   N   V   E
GAT GAG TTT TAC TAT AGC CCT TGG AAT TAT TTT GAC GCT AGA AAT ATT AAA AAT GTT GAA
480                            490
 I   T   N   K   L   A   F   G   P   Q   G   S   P   W   G   T   S   K   L   M
ATC ACC AAT AAA CTT GCT TTT GGA CCT CAA GGA AGT CCT TGG GGC ACA TCA AAA CTT ATG
500                            510
 F   N   N   L   T   L   G   Q   N   A   V   M   D   Y   S   Q   F   S   N   L
TTC AAT AAT CTA ACC CTA GGT CAA AAT GCG GTC ATG GAT TAT AGC CAA TTT TCA AAT TTA
520                            530
 T   I   Q   G   D   F   I   N   N   Q   G   T   I   N   Y   L   V   R   G   G
ACC ATT CAA GGG GAT TTC ATC AAC AAT CAA GGC ACT ATC AAC TAT CTG GTC CGA GGT GGG
540                            550
 K   V   A   T   L   S   V   G   N   A   A   M   M   F   N   N   D   I   D
AAA GTG GCA ACC TTA AGC GTA GGC AAT GCA GCA GCT ATG ATG TTT AAT AAT GAT ATA GAC
560                            570
 S   A   T   G   F   Y   K   P   L   I   K   I   N   S   A   Q   D   L   I   K
AGC GCG ACC GGA TTT TAC AAA CCG CTC ATC AAG ATT AAC AGC GCT CAA GAT CTC ATT AAA
580                            590
 N   T   E   H   V   L   L   K   A   K   I   I   G   Y   G   N   V   S   T   G
AAT ACA GAA CAT GTT TTA TTG AAA GCG AAA ATC ATT GGT TAT GGT AAT GTT TCT ACA GGT
600                            610
 T   N   G   I   S   N   V   N   L   E   E   Q   F   K   E   R   L   A   L   Y
ACC AAT GGC ATT AGT AAT GTT AAT CTA GAA GAG CAA TTC AAA GAG CGC CTA GCC CTT TAT
620                            630
 N   N   N   N   R   M   D   T   C   V   V   R   N   T   D   D   I   K   A   C
AAC AAC AAT AAC CGC ATG GAT ACT TGT GTG GTG CGA AAT ACT GAT GAC ATT AAA GCA TGC
640                            650
 G   M   A   I   G   D   Q   S   M   V   N   N   P   D   N   Y   K   Y   L   I
GGT ATG GCT ATC GGC GAT CAA AGC ATG GTG AAC AAC CCT GAC AAT TAC AAG TAT CTT ATC
660                      668
 G   K   A   W   K   N   I   G   I   OC
GGT AAG GCA TGG AAA AAT ATA GGG ATC TAA TAGGTCGAC
```

FIG. 3B

```
  1                            10                              20
  M   E   F   K   N   G   K   N   K   D   F   S   K   V   T   Q   A   K   S   D
 ATG GAA TTC AAA AAT GGC AAA AAT AAG GAT TTC AGC AAG GTA ACG CAA GCA AAA AGC GAC
                                  30                              40
  L   E   N   S   I   K   D   V   I   F   N   Q   K   I   T   D   K   V   D   D
 CTT GAA AAT TCC ATT AAA GAT GTG ATT TTC AAT CAA AAG ATA ACG GAT AAA GTT GAT GAT
                                  50                              60
  L   N   Q   A   V   S   V   A   K   A   T   G   D   F   S   R   V   E   Q   A
 CTC AAT CAA GCG GTA TCA GTG GCT AAA GCA ACG GGT GAT TTC AGT AGG GTA GAG CAA GCG
                                  70                              80
  L   A   D   L   K   N   F   S   K   E   Q   L   A   Q   Q   A   Q   K   N   E
 TTA GCC GAT CTC AAA AAC TTC TCA AAG GAG CAA TTG GCT CAA CAA GCT CAA AAA AAT GAA
                                  90                             100
  S   L   N   A   G   K   K   S   E   I   Y   Q   S   V   K   N   G   V   N   G
 AGT CTC AAT GCT GGA AAA AAA TCT GAA ATA TAC CAA TCC GTT AAG AAT GGT GTA AAC GGA
                                 110                             120
  T   L   V   G   N   G   L   S   Q   A   E   A   T   T   L   S   K   N   F   S
 ACC CTA GTC GGT AAT GGG TTA TCT CAA GCA GAA GCC ACA ACT CTT TCT AAA AAC TTT TCG
                                 130                             140
  D   I   K   K   E   L   N   A   K   L   F   G   N   F   N   N   N   N   N   N
 GAC ATC AAG AAA GAG TTG AAT GCA AAA CTT TTT GGA AAT TTC AAT AAC AAT AAC AAT AAT
                                 150                             160
  G   L   K   N   S   T   E   P   I   Y   A   K   V   N   K   K   T   G   Q
 GGT CTC AAA AAC AGC ACA GAA CCC ATT TAT GCT AAA GTT AAT AAA AAG AAA ACA GGA CAA
                                 170                             180
  V   A   S   P   E   E   P   I   Y   T   Q   V   A   K   K   V   N   A   K   I
 GTA GCT AGC CCT GAA GAA CCC ATT TAT ACT CAA GTT GCT AAA AAG GTA AAT GCA AAA ATT
                                 190                             200
  D   R   L   N   Q   I   A   S   G   L   G   G   V   G   K   A   A   G   F   P
 GAC CGA CTC AAT CAA ATA GCA AGT GGT TTG GGT GGT GTA GGG AAA GCA GCG GGC TTC CCT
                                 210                             220
  L   K   R   H   D   K   V   D   D   L   S   K   V   G   R   S   V   S   P   E
 TTG AAA AGG CAT GAT AAA GTT GAT GAT CTC AGT AAG GTA GGG CGA TCA GTT AGC CCT GAA
                                 230                             240
  P   I   Y   A   T   I   D   D   L   G   G   P   F   P   L   K   R   H   D   K
 CCC ATT TAT GCT ACG ATT GAT GAT CTC GGC GGA CCT TTC CCT TTG AAA AGG CAT GAT AAA
                                 250                             260
  V   D   D   L   S   K   V   G   L   S   R   N   Q   E   L   A   Q   K   I   D
 GTT GAT GAT CTC AGT AAG GTA GGG CTT TCA AGG AAC CAA GAA TTG GCT CAG AAA ATT GAC
                    268
  N   L   N   Q   A   V   S   E   OC
 AAT CTC AAT CAA GCG GTA TCA GAA TAA TAGTCGAC
```

FIG. 4

SEQUENCE LISTING

<160> NUMBER OF SEQ ID NOS: 4

<210> SEQ ID NO 1
<211> LENGTH: 2018
<212> TYPE: DNA
<213> ORGANISM: Helicobacter pylori
<220> FEATURE:
<221> NAME/KEY: CDS
<222> LOCATION: (3)..(2006)

<400> SEQUENCE: 1

```
cc atg gct aca aag gct gtt tgt gtt ttg aag ggt gac ggc cca gtt         47
   Met Ala Thr Lys Ala Val Cys Val Leu Lys Gly Asp Gly Pro Val
    1               5                  10                  15 caa ggt att att aac ttc gag cag aag gaa agt aat gga cca gtg aag        95
Gln Gly Ile Ile Asn Phe Glu Gln Lys Glu Ser Asn Gly Pro Val Lys
                 20                  25                  30 gtg tgg gga agc att aaa gga ctg act gaa ggc ctg cat gga ttc cat       143
Val Trp Gly Ser Ile Lys Gly Leu Thr Glu Gly Leu His Gly Phe His
             35                  40                  45 gtt cat gag ttt gga gat aat aca gca ggc tgt acc agt gca ggt cct       191
Val His Glu Phe Gly Asp Asn Thr Ala Gly Cys Thr Ser Ala Gly Pro
         50                  55                  60 cac ttt aat cct cta tcc aga aaa cac ggt ggg cca aag gat gaa gag       239
His Phe Asn Pro Leu Ser Arg Lys His Gly Gly Pro Lys Asp Glu Glu
     65                  70                  75 agg cat gtt gga gac ttg ggc aat gtg act gct gac aaa gat ggt gtg       287
Arg His Val Gly Asp Leu Gly Asn Val Thr Ala Asp Lys Asp Gly Val
 80                  85                  90                  95 gcc gat gtg tct att gaa gat tct gtg atc tca ctc tca gga gac cat       335
Ala Asp Val Ser Ile Glu Asp Ser Val Ile Ser Leu Ser Gly Asp His
                100                 105                 110 tgc atc att ggc cgc aca ctg gtg gtc cat gaa aaa gca gat gac ttg       383
Cys Ile Ile Gly Arg Thr Leu Val Val His Glu Lys Ala Asp Asp Leu
            115                 120                 125 ggc aaa ggt gga aat gaa gaa agt aca aag aca gga aac gct gga agt       431
Gly Lys Gly Gly Asn Glu Glu Ser Thr Lys Thr Gly Asn Ala Gly Ser
        130                 135                 140 cgt ttg gct tgt ggt gta att ggg atc gcc cag aat ttg gga att ctc       479
Arg Leu Ala Cys Gly Val Ile Gly Ile Ala Gln Asn Leu Gly Ile Leu
    145                 150                 155 ggc aca ctg gat ttg tgg caa agc gcc ggg tta aac att atc gct cct       527
Gly Thr Leu Asp Leu Trp Gln Ser Ala Gly Leu Asn Ile Ile Ala Pro
160                 165                 170                 175 cca gaa ggt ggc tat aag gat aaa ccc aat aat acc cct tct caa agt       575
Pro Glu Gly Gly Tyr Lys Asp Lys Pro Asn Asn Thr Pro Ser Gln Ser
                180                 185                 190 ggt gct aaa aac gac aaa aat gaa agc gct aaa aac gac aaa caa gag       623
Gly Ala Lys Asn Asp Lys Asn Glu Ser Ala Lys Asn Asp Lys Gln Glu
            195                 200                 205 agc agt caa aat aat agt aac act cag gtc att aac cca ccc aat agt       671
Ser Ser Gln Asn Asn Ser Asn Thr Gln Val Ile Asn Pro Pro Asn Ser
        210                 215                 220
```

-continued

| | |
|---|---|
| gcg caa aaa aca gaa gtt caa ccc acg caa gtc att gat ggg cct ttt<br>Ala Gln Lys Thr Glu Val Gln Pro Thr Gln Val Ile Asp Gly Pro Phe<br>225                    230                    235 | 719 |
| gcg ggc ggc aaa gac acg gtt gtc aat atc aac cgc atc aac act aac<br>Ala Gly Gly Lys Asp Thr Val Val Asn Ile Asn Arg Ile Asn Thr Asn<br>240                    245                    250                    255 | 767 |
| gct gat ggc acg att aga gtg gga ggg ttt aaa gct tct ctt acc acc<br>Ala Asp Gly Thr Ile Arg Val Gly Gly Phe Lys Ala Ser Leu Thr Thr<br>                    260                    265                    270 | 815 |
| aat gcg gct cat ttg cat atc ggc aaa ggc ggt gtc aat ctg tcc aat<br>Asn Ala Ala His Leu His Ile Gly Lys Gly Gly Val Asn Leu Ser Asn<br>                275                    280                    285 | 863 |
| caa gcg agc ggg cgc tct ctt ata gtg gaa aat cta act ggg aat atc<br>Gln Ala Ser Gly Arg Ser Leu Ile Val Glu Asn Leu Thr Gly Asn Ile<br>            290                    295                    300 | 911 |
| acc gtt gat ggg cct tta aga gtg aat aat caa gtg ggt ggc tat gct<br>Thr Val Asp Gly Pro Leu Arg Val Asn Asn Gln Val Gly Gly Tyr Ala<br>305                    310                    315 | 959 |
| ttg gca gga tca agc gcg aat ttt gag ttt aag gct ggt acg gat acc<br>Leu Ala Gly Ser Ser Ala Asn Phe Glu Phe Lys Ala Gly Thr Asp Thr<br>320                    325                    330                    335 | 1007 |
| aaa aac ggc aca gcc act ttt aat aac gat att agt ctg gga aga ttt<br>Lys Asn Gly Thr Ala Thr Phe Asn Asn Asp Ile Ser Leu Gly Arg Phe<br>            340                    345                    350 | 1055 |
| gtg aat tta aag gtg gat gct cat aca gct aat ttt aaa ggt att gat<br>Val Asn Leu Lys Val Asp Ala His Thr Ala Asn Phe Lys Gly Ile Asp<br>                355                    360                    365 | 1103 |
| acg ggt aat ggt ggt ttc aac acc tta gat ttt agt ggc gtt aca gac<br>Thr Gly Asn Gly Gly Phe Asn Thr Leu Asp Phe Ser Gly Val Thr Asp<br>            370                    375                    380 | 1151 |
| aaa gtc aat atc aac aag ctc att acg gct tcc act aat gtg gcc gtt<br>Lys Val Asn Ile Asn Lys Leu Ile Thr Ala Ser Thr Asn Val Ala Val<br>385                    390                    395 | 1199 |
| aaa aac ttc aac att aat gaa ttg att gtt aaa acc aat ggg ata agt<br>Lys Asn Phe Asn Ile Asn Glu Leu Ile Val Lys Thr Asn Gly Ile Ser<br>400                    405                    410                    415 | 1247 |
| gtg ggg gaa tat act cat ttt agc gaa gat ata ggc agt caa tcg cgc<br>Val Gly Glu Tyr Thr His Phe Ser Glu Asp Ile Gly Ser Gln Ser Arg<br>                420                    425                    430 | 1295 |
| atc aat acc gtg cgt ttg gaa act ggc act agg tca ctt ttc tct ggg<br>Ile Asn Thr Val Arg Leu Glu Thr Gly Thr Arg Ser Leu Phe Ser Gly<br>            435                    440                    445 | 1343 |
| ggt gtt aaa ttt aaa ggt ggc gaa aaa ttg gtt ata gat gag ttt tac<br>Gly Val Lys Phe Lys Gly Gly Glu Lys Leu Val Ile Asp Glu Phe Tyr<br>            450                    455                    460 | 1391 |
| tat agc cct tgg aat tat ttt gac gct aga aat att aaa aat gtt gaa<br>Tyr Ser Pro Trp Asn Tyr Phe Asp Ala Arg Asn Ile Lys Asn Val Glu<br>465                    470                    475 | 1439 |
| atc acc aat aaa ctt gct ttt gga cct caa gga agt cct tgg ggc aca<br>Ile Thr Asn Lys Leu Ala Phe Gly Pro Gln Gly Ser Pro Trp Gly Thr<br>480                    485                    490                    495 | 1487 |
| tca aaa ctt atg ttc aat aat cta acc cta ggt caa aat gcg gtc atg<br>Ser Lys Leu Met Phe Asn Asn Leu Thr Leu Gly Gln Asn Ala Val Met<br>                500                    505                    510 | 1535 |
| gat tat agc caa ttt tca aat tta acc att caa ggg gat ttc atc aac<br>Asp Tyr Ser Gln Phe Ser Asn Leu Thr Ile Gln Gly Asp Phe Ile Asn<br>            515                    520                    525 | 1583 |
| aat caa ggc act atc aac tat ctg gtc cga ggt ggg aaa gtg gca acc<br>Asn Gln Gly Thr Ile Asn Tyr Leu Val Arg Gly Gly Lys Val Ala Thr | 1631 |

-continued

```
                  530                 535                 540
tta agc gta ggc aat gca gca gct atg atg ttt aat aat gat ata gac    1679
Leu Ser Val Gly Asn Ala Ala Ala Met Met Phe Asn Asn Asp Ile Asp
        545                 550                 555 agc gcg acc gga ttt tac aaa ccg ctc atc aag att aac agc gct caa    1727
Ser Ala Thr Gly Phe Tyr Lys Pro Leu Ile Lys Ile Asn Ser Ala Gln
560                 565                 570                 575 gat ctc att aaa aat aca gaa cat gtt tta ttg aaa gcg aaa atc att    1775
Asp Leu Ile Lys Asn Thr Glu His Val Leu Leu Lys Ala Lys Ile Ile
                580                 585                 590 ggt tat ggt aat gtt tct aca ggt acc aat ggc att agt aat gtt aat    1823
Gly Tyr Gly Asn Val Ser Thr Gly Thr Asn Gly Ile Ser Asn Val Asn
            595                 600                 605 cta gaa gag caa ttc aaa gag cgc cta gcc ctt tat aac aac aat aac    1871
Leu Glu Glu Gln Phe Lys Glu Arg Leu Ala Leu Tyr Asn Asn Asn Asn
        610                 615                 620 cgc atg gat act tgt gtg gtg cga aat act gat gac att aaa gca tgc    1919
Arg Met Asp Thr Cys Val Val Arg Asn Thr Asp Asp Ile Lys Ala Cys
    625                 630                 635 ggt atg gct atc ggc gat caa agc atg gtg aac aac cct gac aat tac    1967
Gly Met Ala Ile Gly Asp Gln Ser Met Val Asn Asn Pro Asp Asn Tyr
640                 645                 650                 655 aag tat ctt atc ggt aag gca tgg aaa aat ata ggg atc taataggtcg ac  2018
Lys Tyr Leu Ile Gly Lys Ala Trp Lys Asn Ile Gly Ile
                660                 665
```

<210> SEQ ID NO 2
<211> LENGTH: 668
<212> TYPE: PRT
<213> ORGANISM: Helicobacter pylori

<400> SEQUENCE: 2

```
Met Ala Thr Lys Ala Val Cys Val Leu Lys Gly Asp Gly Pro Val Gln
1               5                  10                  15

Gly Ile Ile Asn Phe Glu Gln Lys Glu Ser Asn Gly Pro Val Lys Val
            20                  25                  30

Trp Gly Ser Ile Lys Gly Leu Thr Glu Gly Leu His Gly Phe His Val
        35                  40                  45

His Glu Phe Gly Asp Asn Thr Ala Gly Cys Thr Ser Ala Gly Pro His
    50                  55                  60

Phe Asn Pro Leu Ser Arg Lys His Gly Pro Lys Asp Glu Glu Arg
65                  70                  75                  80

His Val Gly Asp Leu Gly Asn Val Thr Ala Asp Lys Asp Gly Val Ala
                85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln Asn Leu Gly Ile Leu Gly
145                 150                 155                 160

Thr Leu Asp Leu Trp Gln Ser Ala Gly Leu Asn Ile Ile Ala Pro Pro
                165                 170                 175

Glu Gly Gly Tyr Lys Asp Lys Pro Asn Asn Thr Pro Ser Gln Ser Gly
            180                 185                 190

Ala Lys Asn Asp Lys Asn Glu Ser Ala Lys Asn Asp Lys Gln Glu Ser
```

```
            195                 200                 205
Ser Gln Asn Asn Ser Asn Thr Gln Val Ile Asn Pro Pro Asn Ser Ala
            210                 215                 220

Gln Lys Thr Glu Val Gln Pro Thr Gln Val Ile Asp Gly Pro Phe Ala
225                 230                 235                 240

Gly Gly Lys Asp Thr Val Val Asn Ile Asn Arg Ile Asn Thr Asn Ala
                    245                 250                 255

Asp Gly Thr Ile Arg Val Gly Gly Phe Lys Ala Ser Leu Thr Thr Asn
                260                 265                 270

Ala Ala His Leu His Ile Gly Lys Gly Val Asn Leu Ser Asn Gln
            275                 280                 285

Ala Ser Gly Arg Ser Leu Ile Val Glu Asn Leu Thr Gly Asn Ile Thr
    290                 295                 300

Val Asp Gly Pro Leu Arg Val Asn Asn Gln Val Gly Gly Tyr Ala Leu
305                 310                 315                 320

Ala Gly Ser Ser Ala Asn Phe Glu Phe Lys Ala Gly Thr Asp Thr Lys
                325                 330                 335

Asn Gly Thr Ala Thr Phe Asn Asn Asp Ile Ser Leu Gly Arg Phe Val
                340                 345                 350

Asn Leu Lys Val Asp Ala His Thr Ala Asn Phe Lys Gly Ile Asp Thr
            355                 360                 365

Gly Asn Gly Gly Phe Asn Thr Leu Asp Phe Ser Gly Val Thr Asp Lys
        370                 375                 380

Val Asn Ile Asn Lys Leu Ile Thr Ala Ser Thr Asn Val Ala Val Lys
385                 390                 395                 400

Asn Phe Asn Ile Asn Glu Leu Ile Val Lys Thr Asn Gly Ile Ser Val
                405                 410                 415

Gly Glu Tyr Thr His Phe Ser Glu Asp Ile Gly Ser Gln Ser Arg Ile
                420                 425                 430

Asn Thr Val Arg Leu Glu Thr Gly Thr Arg Ser Leu Phe Ser Gly Gly
            435                 440                 445

Val Lys Phe Lys Gly Gly Glu Lys Leu Val Ile Asp Glu Phe Tyr Tyr
    450                 455                 460

Ser Pro Trp Asn Tyr Phe Asp Ala Arg Asn Ile Lys Asn Val Glu Ile
465                 470                 475                 480

Thr Asn Lys Leu Ala Phe Gly Pro Gln Gly Ser Pro Trp Gly Thr Ser
                485                 490                 495

Lys Leu Met Phe Asn Asn Leu Thr Leu Gly Gln Asn Ala Val Met Asp
                500                 505                 510

Tyr Ser Gln Phe Ser Asn Leu Thr Ile Gln Gly Asp Phe Ile Asn Asn
            515                 520                 525

Gln Gly Thr Ile Asn Tyr Leu Val Arg Gly Gly Lys Val Ala Thr Leu
        530                 535                 540

Ser Val Gly Asn Ala Ala Ala Met Met Phe Asn Asn Asp Ile Asp Ser
545                 550                 555                 560

Ala Thr Gly Phe Tyr Lys Pro Leu Ile Lys Ile Asn Ser Ala Gln Asp
                565                 570                 575

Leu Ile Lys Asn Thr Glu His Val Leu Leu Lys Ala Lys Ile Ile Gly
                580                 585                 590

Tyr Gly Asn Val Ser Thr Gly Thr Asn Gly Ile Ser Asn Val Asn Leu
            595                 600                 605

Glu Glu Gln Phe Lys Glu Arg Leu Ala Leu Tyr Asn Asn Asn Asn Arg
        610                 615                 620
```

```
Met Asp Thr Cys Val Val Arg Asn Thr Asp Asp Ile Lys Ala Cys Gly
625                 630                 635                 640

Met Ala Ile Gly Asp Gln Ser Met Val Asn Asn Pro Asp Asn Tyr Lys
            645                 650                 655

Tyr Leu Ile Gly Lys Ala Trp Lys Asn Ile Gly Ile
            660                 665

<210> SEQ ID NO 3
<211> LENGTH: 815
<212> TYPE: DNA
<213> ORGANISM: Helicobacter pylori
<220> FEATURE:
<221> NAME/KEY: CDS
<222> LOCATION: (1)..(804)

<400> SEQUENCE: 3 atg gaa ttc aaa aat ggc aaa aat aag gat ttc agc aag gta acg caa    48
Met Glu Phe Lys Asn Gly Lys Asn Lys Asp Phe Ser Lys Val Thr Gln
1               5                   10                  15 gca aaa agc gac ctt gaa aat tcc att aaa gat gtg att ttc aat caa    96
Ala Lys Ser Asp Leu Glu Asn Ser Ile Lys Asp Val Ile Phe Asn Gln
            20                  25                  30 aag ata acg gat aaa gtt gat gat ctc aat caa gcg gta tca gtg gct   144
Lys Ile Thr Asp Lys Val Asp Asp Leu Asn Gln Ala Val Ser Val Ala
        35                  40                  45 aaa gca acg ggt gat ttc agt agg gta gag caa gcg tta gcc gat ctc   192
Lys Ala Thr Gly Asp Phe Ser Arg Val Glu Gln Ala Leu Ala Asp Leu
    50                  55                  60 aaa aac ttc tca aag gag caa ttg gct caa caa gct caa aaa aat gaa   240
Lys Asn Phe Ser Lys Glu Gln Leu Ala Gln Gln Ala Gln Lys Asn Glu
65                  70                  75                  80 agt ctc aat gct gga aaa aaa tct gaa ata tac caa tcc gtt aag aat   288
Ser Leu Asn Ala Gly Lys Lys Ser Glu Ile Tyr Gln Ser Val Lys Asn
                85                  90                  95 ggt gta aac gga acc cta gtc ggt aat ggg tta tct caa gca gaa gcc   336
Gly Val Asn Gly Thr Leu Val Gly Asn Gly Leu Ser Gln Ala Glu Ala
            100                 105                 110 aca act ctt tct aaa aac ttt tcg gac atc aag aaa gag ttg aat gca   384
Thr Thr Leu Ser Lys Asn Phe Ser Asp Ile Lys Lys Glu Leu Asn Ala
        115                 120                 125 aaa ctt ttt gga aat ttc aat aac aat aac aat aat ggt ctc aaa aac   432
Lys Leu Phe Gly Asn Phe Asn Asn Asn Asn Asn Asn Gly Leu Lys Asn
    130                 135                 140 agc aca gaa ccc att tat gct aaa gtt aat aaa aag aaa aca gga caa   480
Ser Thr Glu Pro Ile Tyr Ala Lys Val Asn Lys Lys Lys Thr Gly Gln
145                 150                 155                 160 gta gct agc cct gaa gaa ccc att tat act caa gtt gct aaa aag gta   528
Val Ala Ser Pro Glu Glu Pro Ile Tyr Thr Gln Val Ala Lys Lys Val
                165                 170                 175 aat gca aaa att gac cga ctc aat caa ata gca agt ggt ttg ggt ggt   576
Asn Ala Lys Ile Asp Arg Leu Asn Gln Ile Ala Ser Gly Leu Gly Gly
            180                 185                 190 gta ggg aaa gca gcg ggc ttc cct ttg aaa agg cat gat aaa gtt gat   624
Val Gly Lys Ala Ala Gly Phe Pro Leu Lys Arg His Asp Lys Val Asp
        195                 200                 205 gat ctc agt aag gta ggg cga tca gtt agc cct gaa ccc att tat gct   672
Asp Leu Ser Lys Val Gly Arg Ser Val Ser Pro Glu Pro Ile Tyr Ala
    210                 215                 220 acg att gat gat ctc ggc gga cct ttc cct ttg aaa agg cat gat aaa   720
Thr Ile Asp Asp Leu Gly Gly Pro Phe Pro Leu Lys Arg His Asp Lys
```

```
                    225                 230                 235                 240
gtt gat gat ctc agt aag gta ggg ctt tca agg aac caa gaa ttg gct        768
Val Asp Asp Leu Ser Lys Val Gly Leu Ser Arg Asn Gln Glu Leu Ala
                    245                 250                 255 cag aaa att gac aat ctc aat caa gcg gta tca gaa taatagtcga c           815
Gln Lys Ile Asp Asn Leu Asn Gln Ala Val Ser Glu
                    260                 265

<210> SEQ ID NO 4
<211> LENGTH: 268
<212> TYPE: PRT
<213> ORGANISM: Helicobacter pylori

<400> SEQUENCE: 4

Met Glu Phe Lys Asn Gly Lys Asn Lys Asp Phe Ser Lys Val Thr Gln
  1               5                  10                  15

Ala Lys Ser Asp Leu Glu Asn Ser Ile Lys Asp Val Ile Phe Asn Gln
                 20                  25                  30

Lys Ile Thr Asp Lys Val Asp Asp Leu Asn Gln Ala Val Ser Val Ala
             35                  40                  45

Lys Ala Thr Gly Asp Phe Ser Arg Val Glu Gln Ala Leu Ala Asp Leu
         50                  55                  60

Lys Asn Phe Ser Lys Glu Gln Leu Ala Gln Gln Ala Gln Lys Asn Glu
 65                  70                  75                  80

Ser Leu Asn Ala Gly Lys Lys Ser Glu Ile Tyr Gln Ser Val Lys Asn
                 85                  90                  95

Gly Val Asn Gly Thr Leu Val Gly Asn Gly Leu Ser Gln Ala Glu Ala
            100                 105                 110

Thr Thr Leu Ser Lys Asn Phe Ser Asp Ile Lys Lys Glu Leu Asn Ala
        115                 120                 125

Lys Leu Phe Gly Asn Phe Asn Asn Asn Asn Asn Gly Leu Lys Asn
    130                 135                 140

Ser Thr Glu Pro Ile Tyr Ala Lys Val Asn Lys Lys Thr Gly Gln
145                 150                 155                 160

Val Ala Ser Pro Glu Glu Pro Ile Tyr Thr Gln Val Ala Lys Lys Val
                165                 170                 175

Asn Ala Lys Ile Asp Arg Leu Asn Gln Ile Ala Ser Gly Leu Gly Gly
            180                 185                 190

Val Gly Lys Ala Ala Gly Phe Pro Leu Lys Arg His Asp Lys Val Asp
        195                 200                 205

Asp Leu Ser Lys Val Gly Arg Ser Val Ser Pro Glu Pro Ile Tyr Ala
    210                 215                 220

Thr Ile Asp Asp Leu Gly Gly Pro Phe Pro Leu Lys Arg His Asp Lys
225                 230                 235                 240

Val Asp Asp Leu Ser Lys Val Gly Leu Ser Arg Asn Gln Glu Leu Ala
                245                 250                 255

Gln Lys Ile Asp Asn Leu Asn Gln Ala Val Ser Glu
            260                 265
```

HELICOBACTER PYLORI DIAGNOSTICS

CROSS-REFERENCE TO RELATED APPLICATION

This application is related to provisional patent application Ser. No. 60/033,707, filed Dec. 19, 1996, from which priority is claimed under 35 USC §119(e) (1) and which is incorporated herein by reference in its entirety.

BACKGROUND OF THE INVENTION

TECHNICAL FIELD

The present invention pertains generally to bacterial diagnostic techniques. In particular, the invention relates to methods for accurately detecting *Helicobacter pylori* infection in a biological sample and for monitoring the course of antibiotic treatment in a patient with an *H. pylori* infection.

BACKGROUND OF THE INVENTION

*Helicobacter pylori*, originally named *Campylobacter pylori*, is a curved, microaerophilic, gram-negative bacterium that exhibits high urease and catalase activity. Recent studies suggest that *H. pylori* infection may be either a cause of, or a cofactor in, type B gastritis, peptic ulcers, and gastric tumors. See, e.g., Blaser, *Gastroenterology* (1987) 93:371–383; Dooley et al., *New Eng. J. Med.* (1989) 321:1562–1566; Personnet et al., *New Eng. J. Med.* (1991) 325:1127–1131. In this regard, *H. pylori* colonizes the human gastric mucosa and causes an infection that can persist for decades. Many people with this condition are asymptomatic but are nonetheless at a considerable risk of developing peptic ulcers and/or gastric adenocarcinomas. For a review of *H. pylori* and its role in gastric disease, see, Telford et al., *Trends in Biotech.* (1994) 12:420–426 and Blaser, M. J., *Scientific American* (February 1996):104–107.

*H. pylori* bacteria are divided into two groups, Type I and Type II, based on the presence or absence of specific proteins. In this regard, *H. pylori* produces several factors that function to establish and maintain infection. For example, both Type I and Type II bacteria include flagella that aid in mobility in the viscous mucus layer of the stomach. Both types of bacteria also produce ureases, presumably to neutralize the acid environment of the stomach. Additionally, the two types of bacteria produce a number of adhesins for tissue-specific colonization. On the other hand, only *H. pylori* Type I strains produce a potent cytotoxin, known as VacA or CT, as well as a surface-exposed immunodominant antigen which is associated with cytotoxin expression, known as CagA, CAI antigen or tagA. For descriptions of VacA and CagA, see, e.g., International Publication No. WO 93/18150, published 16 Sep. 1993.

Patients with duodenal ulcers have been shown to produce antibodies to VacA and CagA and antibody titers appear to correlate with the severity of the disease. For example, in one study, more than 95% of patients with duodenal ulcer or duodenitis, and more than 70% of patients suffering from gastric ulcer, were found to be CagA seropositive. Telford et al., *Trends in Biotech.* (1994) 12:420–426. Furthermore, a correlation has been shown between CagA serum response and gastric adenocarcinoma. Telford et al., supra. Additionally, only cytotoxic strains are able to induce gastric lesions in a laboratory animal model. See, e.g., Telford et al., *J. Exp. Med.* (1994) 179:1653–1658. Thus, it is believed that only individuals infected with *H. pylori* Type I strains develop severe disease.

Several assays have been developed for the diagnosis of *H. pylori* infection. These assays, unfortunately, suffer from several drawbacks. For example, bacterial culture assays have been described for the detection of *H. pylori*. U.S. Pat. No. 5,498,528 describes such a method for detecting *H. pylori* in saliva. The assay requires incubating the test sample with a culture medium that supports the selective growth of *H. pylori*. The presence of the bacterium is detected by the activity of the enzyme urease which, as described above, is produced by *H. pylori*. Urease catalyzes the conversion of urea to ammonium causing an increase in the pH of the culture medium. The pH change can be detected by a color change to the medium due to the presence of a pH sensitive indicator. However, the assay is time consuming since the bacteria require a number of days for growth. The assay is also inconvenient and bacterial samples may degrade or become contaminated during transport to the laboratory.

Antibody detection tests provide an alternative to bacterial culture. In this regard, subjects colonized with *H. pylori* mount a humoral immune response and produce antibodies to the bacterium that can be used as a basis for diagnosis. IgA antibodies are found in gastric fluid while IgG antibodies are found in the circulation. However, such tests can suffer from a lack of specificity since *H. pylori* appears to be antigenically cross-reactive with *Campylobacter jejuni* and *C. coli*.

U.S. Pat. No. 4,882,271 describes an *H. pylori* assay that utilizes high molecular weight cell-associated proteins, on the order of 300 kDa to 700 kDa, having urease activity, in an enzyme-linked immunosorbent assay (ELISA), in an attempt to circumvent the problems with cross-reactivity.

International Publication No. WO 96/12965, published 2 May 1996, describes an immunoblot assay where a serological sample is reacted with two antigen components having molecular weights of 19.5 kDa, 26.5 kDa or 30 kDa, or alternatively, any one antigen component corresponding to a molecular weight of 35 kDa, 89 kDa, 116 kDa or 180 kDa. It is postulated by the inventors that the 19.5 kDa protein is a ferritin-like protein, the 26.5 and 30 kDa proteins are ureases, the 89 kDa protein is VacA, and that the 116 kDa protein is CagA. The 35 kDa and 180 kDa were uncharacterized.

Finally, European Patent Publication 329,570, published 23 Aug. 1989, describes immunoassays for *H. pylori* infection using pooled suspensions of sonicates of several *H. pylori* strains, as well as immunoassays using purified *H. pylori* flagellae.

Although faster and more sensitive than bacterial culture, antibody detection tests, such as those described above, can give false positive and negative results and generally do not distinguish between *H. pylori* Type I and Type II infection. Thus, an additional test must be conducted to determine whether the infection is due to *H. pylori* Type I or Type II.

Accordingly, the wide spread availability of an accurate and efficient assay for *H. pylori* infection that readily distinguishes between Type I and Type II infection, would be important for the diagnosis of infection in both symptomatic and asymptomatic individuals.

SUMMARY OF THE INVENTION

The present invention provides a simple, extremely accurate and efficient method for diagnosing *H. pylori* infection, as well as for distinguishing between *H. pylori* Type I and *H. pylori* Type II infections. Thus, the method provides a technique for screening for individuals with *H. pylori* Type I infection. If Type I infection is detected, the individual can be given antibiotics to treat or prevent type B gastritis, peptic ulcers, and gastric tumors. The method is also useful for monitoring the course of treatment in a patient with an *H. pylori* infection. The assay method utilizes both type-common antigens, as well as particular type-specific antigens from the bacterium.

Accordingly, in one embodiment, the subject invention is directed to a method of detecting *H. pylori* infection comprising:

(a) providing a biological sample;

(b) reacting the biological sample with one or more *H. pylori* type-common antigens and reacting the biological sample with one or more purified type-specific *H. pylori* Type I antigens, under conditions which allow *H. pylori* antibodies, when present in the biological sample, to bind with the *H. pylori* type-common antigens and/or the type-specific antigens, thereby detecting the presence or absence of *H. pylori* infection.

In other embodiments, the invention is directed to a method for distinguishing between *H. pylori* Type I and *H. pylori* Type II infection in a biological sample, or a method of monitoring a subject undergoing therapy for an *Helicobacter pylori* infection, the methods comprising:

(a) immobilizing one or more *H. pylori* type-common antigens, e.g., an *H. pylori* lysate and/or *H. pylori* urease, and immobilizing one or more purified type-specific *H. pylori* Type I antigens, e.g., *H. pylori* VacA and/or *H. pylori* CagA, on a nitrocellulose strip;

(b) contacting the nitrocellulose strip from step (a) with the biological sample under conditions which allow anti-*H. pylori* Type I and anti-*H. pylori* Type II antibodies, when present in the biological sample, to bind with *H. pylori* type-common antigens present in the lysate and/or the type-specific *H. pylori* Type I antigens;

(c) removing unbound antibodies;

(d) providing a detectably labeled anti-human immunoglobulin antibody; and (e) detecting the presence or absence of bound anti-human immunoglobulin antibodies in the biological sample, thereby detecting the presence or absence of *H. pylori* Type I or Type II infection.

In particularly preferred embodiments, the biological sample is a human serum sample.

In yet further embodiments, the invention is directed to membrane supports comprising one or more *H. pylori* type-common antigens and one or more purified type-specific *H. pylori* Type I antigens, discretely immobilized thereon.

In another embodiment, the invention is directed to a nitrocellulose support comprising:

(a) an *H. pylori* Type I VacA polypeptide;

(b) an *H. pylori* Type I CagA polypeptide;

(c) an *H. pylori* urease; and (d) a human IgG, wherein the *H. pylori* polypeptides and urease, and the human IgG, are immobilized as discrete bands on said nitrocellulose support.

In a further embodiment, the invention is directed to a nitrocellulose support comprising:

(a) an *H. pylori* Type I VacA polypeptide;

(b) an *H. pylori* Type I CagA polypeptide;

(c) an *H. pylori* lysate; and (d) a human IgG, wherein the *H. pylori* polypeptides and lysate, and the human IgG, are immobilized as discrete bands on said nitrocellulose support.

In other embodiments, the invention is directed to immunodiagnostic test kits for detecting *H. pylori* infection. The kits comprise (a) one or more *H. pylori* type-common antigens; (b) one or more purified type-specific *H. pylori* Type I antigens; and (c) instructions for conducting the immunodiagnostic test.

In still further embodiments, the invention is directed to an immunodiagnostic test kit for distinguishing between *H. pylori* Type I and *H. pylori* Type II infection in a biological sample, or for monitoring a subject undergoing therapy for an *Helicobacter pylori* infection. The test kit comprises (a) one or more *H. pylori* type-common antigens immobilized on a nitrocellulose strip, e.g., an *H. pylori* lysate and/or *H. pylori* urease; (b) one or more purified type-specific *H. pylori* Type I antigens, e.g., *H. pylori* VacA and/or *H. pylori* CagA, immobilized on a nitrocellulose strip; and (c) instructions for conducting the immunodiagnostic test.

These and other embodiments of the present invention will readily occur to those of ordinary skill in the art in view of the disclosure herein.

BRIEF DESCRIPTION OF THE FIGURES

FIGS. 3A–3B (SEQ ID NOS: 1 and 2) show the nucleotide sequence and corresponding amino acid sequence for the *H. pylori* VacA antigen used in the SIAs described in the examples.

FIG. 4 (SEQ ID NO: 3 and 4) shows the nucleotide sequence and corresponding amino acid sequence for the *H. pylori* CagA antigen used in the SIAs described in the examples.

DETAILED DESCRIPTION OF THE INVENTION

Figure 1:
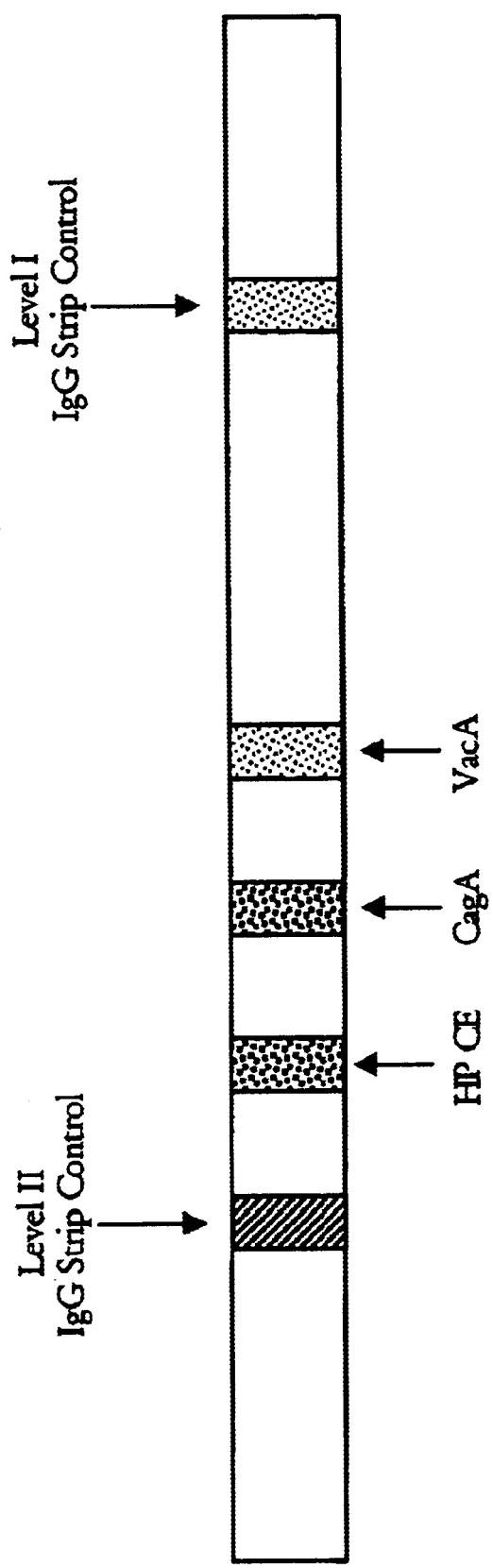
FIG. 1 depicts a representative test strip for use in a strip immunoblot assay (SIA). Human IgG is used as an internal control at two different levels (Level I, low control; and Level II, high control). CagA and VacA are used as the type-specific *H. pylori* Type I antigens and HP CE denotes the *H. pylori* lysate which contains type-common antigens.

The practice of the present invention will employ, unless otherwise indicated, conventional methods of immunology, microbiology, molecular biology and recombinant DNA techniques within the skill of the art. Such techniques are explained fully in the literature. See, e.g., Sambrook, et al., *Molecular Cloning: A Laboratory Manual* (2nd Edition, 1989); *DNA Cloning: A Practical Approach*, vol. I & II (D. Glover, ed.); *Methods In Enzymology* (S. Colowick and N. Kaplan eds., Academic Press, Inc.); and *Handbook of Experimental Immunology*, Vols. I–IV (D. M. Weir and C. C. Blackwell eds., Blackwell Scientific Publications).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Additionally, standard abbreviations for nucleotides and amino acids are used in this specification.

I. Definitions

In describing the present invention, the following terms will be employed, and are intended to be defined as indicated below.

By "an *H. pylori* lysate" is meant an extract or lysate derived from an *H. pylori* Type I or Type II whole bacterium which includes one or more *H. pylori* polypeptides, as defined below, that reacts with antibodies generated against both of *H. pylori* Type I and *H. pylori* Type II. Such polypeptides are termed "type-common" antigens herein. Thus the term "lysate" as used herein refers to crude extracts that contain several *H. pylori* antigens, so long as at least one of the antigens present in the lysate is a type-common antigen. The lysate can be augmented with additional purified type-common and/or type-specific antigens. The term also denotes relatively purified compositions derived from such crude lysates which include only one or few such type-common antigens. Such lysates are prepared using techniques well known in the art, described further below.

Representative antigens that may be present in such lysates, either alone or in combination, include one or more type-common epitopes derived from the *H. pylori* adhesins such as, but not limited to, a 20 kDa N-acetyl-neuraminillactose-binding fibrillar haemagglutinin (HpaA), a 63 kDa protein that binds phosphatidylethanolamine and gangliotetraosyl ceramide, and a conserved fimbrial pilus-like structure. See, e.g., Telford et al., *Trends in Biotech.* (1994) 12:420–426 for a description of these antigens. Other type-common antigens that may be present in the lysate include one or more type-common epitopes derived from any of the various flagellins such as the major flagellin, FlaA and the minor flagellin, FlaB. In this regard, the flagella of *H. pylori* are composed of FlaA and FlaB, each with a molecular weight of approximately 53 kDa. Either or both of FlaA and/or FlaB may be used as a source of type-common antigens for use with the present invention. Another representative type-common antigen includes *H. pylori* urease which is associated with the outer membrane and the periplasmic space of the bacterium. The holoenzyme is a large complex made up of two subunits of 26.5 kDa (UreA) and 61 kDa (UreB), respectively. Type-common epitopes derived from the holoenzyme, either of the subunits, or a combination of the three, can be present as the type-common antigen(s). Another representative type-common antigen that may be present in the lysate or used in further purified form includes the an *H. pylori* heat shock protein known as "hsp60." The DNA and corresponding amino acid sequences for hsp60 are known. See, e.g., International Publication No. WO 93/18150, published 16 Sep. 1993. The full-length hsp60 antigen shown has about 546 amino acids and a molecular weight of about 58 kDa. It is to be understood that the lysate can also include other type-common antigens not specifically described herein.

By a "type-specific *H. pylori* Type I antigen" is meant a polypeptide, as defined below, derived from *H. pylori* Type I which reacts predominantly with antibodies against *H. pylori* Type I, but not with antibodies against *H. pylori* Type II. Representative type-specific *H. pylori* Type I antigens include: *H. pylori* VacA, also known as CT; and *H. pylori* CagA, also known as CAI antigen and tagA; and epitopes from these antigens which are capable of reacting with antibodies against *H. pylori* Type I but not *H. pylori* Type II. Both VacA and CagA are discussed further below. It is to be understood that other type-specific *H. pylori* Type I antigens, not specifically described herein, are also captured by this definition.

The term "polypeptide" when used with reference to a type-common or type-specific *H. pylori* antigen, such as VacA, CagA or any of the other type-specific or type common antigens described above, refers to a VacA, CagA etc., whether native, recombinant or synthetic, which is derived from any of the various *H. pylori* strains. In the case of type-specific *H. pylori* Type I antigens, the polypeptide will be derived from an *H. pylori* Type I strain. In the case of a type-common antigen, the polypeptide may be derived from either of *H. pylori* Type I or Type II. The polypeptide need not include the full-length amino acid sequence of the reference molecule but can include only so much of the molecule as necessary in order for the polypeptide to react with the appropriate *H. pylori* antibodies. Thus, only one or few epitopes of the reference molecule need be present. Furthermore, the polypeptide may comprise a fusion protein between the full-length reference molecule or a fragment of the reference molecule, and another protein that does not disrupt the reactivity of the *H. pylori* polypeptide. It is readily apparent that the polypeptide may therefore comprise the full-length sequence, fragments, truncated and partial sequences, as well as analogs and precursor forms of the reference molecule. The term also intends deletions, additions and substitutions to the reference sequence, so long as the polypeptide retains the ability to react with *H. pylori* antibodies.

In this regard, particularly preferred substitutions will generally be conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. Proteins having substantially the same amino acid sequence as the reference molecule, but possessing minor amino acid substitutions that do not substantially affect the antibody binding capabilities of the protein, are therefore within the definition of the reference polypeptide.

By "VacA polypeptide" is meant a polypeptide as defined above which is derived from the antigen known as the *H. pylori* Type I Cytotoxin and which reacts predominantly with antibodies against *H. pylori* Type I, but not *H. pylori* Type II. The VacA protein induces vacuolization in epithelial cells in tissue culture and causes extensive tissue damage and ulceration when administered orally to mice. The DNA and corresponding amino acid sequences for VacA are known and reported in, e.g., International Publication No. WO 93/18150, published 16 Sep. 1993. The gene for the VacA polypeptide encodes a precursor of about 140 kDa that is processed to an active molecule of about 90–100 kDa. This molecule, in turn, is slowly proteolytically cleaved to generate two fragments that copurify with the intact 90 kDa molecule. See, Telford et al., *Trends in Biotech.* (1994) 12:420–426. Thus, the definition of "VacA polypeptide" as used herein includes the precursor protein, as well as the processed active molecule, proteolytic fragments thereof or portions or muteins thereof, which retain specific reactivity with antibodies present in a biological sample from an individual with *H. pylori* Type I infection. For example, the VacA polypeptide depicted in FIGS. 3A–3B and used in assays described herein includes a VacA fragment from Gly-311 to Ile-819, inclusive, of the full-length molecule, fused by a linker sequence of five amino acids to 154 amino acids of human SOD to facilitate recombinant expression.

By "CagA polypeptide" is meant a polypeptide as defined above which is derived from the *H. pylori* Type I cytotoxin associated immunodominant antigen and which reacts predominantly with antibodies against *H. pylori* Type I, but not *H. pylori* Type II. CagA is expressed on the bacterial surface. The DNA and corresponding amino acid sequences for CagA are known. See, e.g., International Publication No. WO 93/18150, published 16 Sep. 1993. The full-length CagA antigen described therein includes about 1147 amino acids with a predicted molecular weight of about 128 kDa. The native protein shows interstrain size variability due to the presence of a variable number of repeats of a 102 bp DNA segment that encodes repeats of a proline-rich amino acid sequence. See, Covacci et al., *Proc. Natl. Acad. Sci. USA* (1993) 90:5791–5795. Accordingly, the reported molecular weight of CagA ranges from about 120–135 kDa. Hence, the definition of "CagA polypeptide" as used herein includes any of the various CagA variants, fragments thereof and muteins thereof, which retain the ability to react with antibodies in a biological sample from an individual with *H. pylori* Type I infection but does not substantially react with antibodies generated against *H. pylori* Type II. For example, the CagA polypeptide depicted in FIG. 4 and used in assays described herein is a truncated protein of 268 amino acids and includes Glu-748 to Glu-1015, inclusive, of the full-length molecule.

By "epitope" is meant a site on an antigen to which specific B cells and T cells respond. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8–10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology. See, also, Geysen et al., *Proc. Natl. Acad. Sci. USA* (1984) 81:3998–4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709–715 (technique for identifying peptides with high affinity for a given antibody). Antibodies that recognize the same epitope can be identified in a simple immunoassay showing the ability of one antibody to block the binding of another antibody to a target antigen.

A "purified" protein or polypeptide is a protein which is recombinantly or synthetically produced, or isolated from its natural host, such that the amount of protein present in a composition is substantially higher than that present in a crude preparation. In general, a purified protein will be at least about 50% homogeneous and more preferably at least about 80% to 90% homogeneous.

As used herein, a "biological sample" refers to a sample of tissue or fluid isolated from an individual, including but not limited to, for example, blood, plasma, serum, fecal matter, urine, bone marrow, bile, spinal fluid, lymph fluid, samples of the skin, external secretions of the skin, respiratory, intestinal, and genitourinary tracts, samples derived from the gastric epithelium and gastric mucosa, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, acradimum esters, NADPH and α-β-galactosidase.

II. Modes of Carrying Out the Invention

The present invention is based on the discovery of novel diagnostic methods for accurately detecting *H. pylori* infection and for discriminating between *H. pylori* Type I and *H. pylori* Type II infection. The methods utilize one or more *H. pylori* type-common antigens, either purified or present in lysates derived from the bacterium, as well as purified type-specific *H. pylori* antigens. The use of both type-common and type-specific antigens reduces the incidence of false positive results. The methods can be practiced in a simple one-step assay format which allows for both detection of infection, as well as identification of the type of infection present, in a single assay. The method can also be practiced in two steps wherein the sample is first reacted with the *H. pylori* type-common antigens and if positive, reacted with one or more type-specific Type I antigens. The methods can also employ type-specific Type II antigens.

More particularly, the use of the *H. pylori* type-common antigens allows the diagnosis of *H. pylori* infection in general. The presence of one or more type-specific antigens allows determination of the bacterial type, i.e., whether the infection is caused by *H. pylori* Type I and/or *H. pylori* Type II. Due to the presence of the *H. pylori* type-common antigens, positive results will occur even in untypable samples. Hence, the incidence of false negatives is reduced. Furthermore, if *H. pylori* Type I infection is present, the individual can be administered antibiotics to treat or prevent type B gastritis, peptic ulcers, and gastric tumors.

Furthermore, the assays described herein are useful for monitoring the course of treatment in a subject to determine whether antibiotic therapy is effective.

The antigens for use in the subject diagnostic techniques can be produced using a variety of techniques. For example, the type-common antigens can be provided in a lysate that can be obtained using methods well known in the art. Generally, such methods entail extracting type-common proteins from either *H. pylori* Type I or Type II bacteria using sonication, pressure disintegration, detergent extraction, fractionation, and the like. Type-common antigens present in such lysates can be further purified if desired, using standard purification techniques. *H. pylori* strains for use in such methods are readily available from several sources including the American Type Culture Collection (ATCC, Rockville, Md.). For example, ATCC strain designations NCTC 11637, 11639 and 11916, will find use as a source of the lysate. Other useful strains are known in the art.

The type-specific *H. pylori* Type I antigens can also be obtained using standard purification techniques. In this regard, particular antigens can be isolated from Type I *H. pylori* ulcer-producing strains using standard purification techniques such as column chromatography, electrophoresis, HPLC, immunoadsorbent techniques, affinity chromatography and immunoprecipitation. See, e.g., International Publication No. WO 96/12965, published 2 May 1996, for a description of the purification of several antigens from *H. pylori*. For example, ATCC strain designation NCTC 11916 is a Type I ulcer-producing strain of *H. pylori* and can therefore be used as a source for one or more type-specific antigens for use in the subject invention.

The *H. pylori* antigens can also be generated using recombinant methods, well known in the art. In this regard, oligonucleotide probes can be devised based on the known sequences of the *H. pylori* genome and used to probe genomic or cDNA libraries for *H. pylori* genes encoding for the antigens useful in the present invention. The genes can then be further isolated using standard techniques and, if desired, restriction enzymes employed to mutate the gene at desired portions of the full-length sequence.

Similarly, *H. pylori* genes can be isolated directly from bacterial cells using known techniques, such as phenol extraction, and the sequence can be further manipulated to produce any desired alterations. See, e.g., Sambrook et al., supra, for a description of techniques used to obtain and isolate DNA. Finally, the genes encoding the *H. pylori* antigens can be produced synthetically, based on the known sequences. The nucleotide sequence can be designed with the appropriate codons for the particular amino acid sequence desired. In general, one will select preferred codons for the intended host in which the sequence will be expressed. The complete sequence is generally assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J. Biol. Chem.* (1984) 259:6311.

Once coding sequences for the desired polypeptides have been isolated or synthesized, they can be cloned into any suitable vector or replicon for expression in a variety of systems, including insect, mammalian, bacterial, viral and yeast expression systems, all well known in the art. In particular, host cells are transformed with expression vectors which include control sequences operably linked to the desired coding sequence.

The control sequences will be compatible with the particular host cell used. For example, typical promoters for mammalian cell expression include the SV40 early promoter, mouse mammary tumor virus LTR promoter, adenovirus major late promoter (Ad MLP), and herpes simplex virus promoter, among others. Other non-viral promoters, such as a promoter derived from the murine metallothionein gene, will also find use in mammalian constructs. Mammalian expression may be either constitutive or regulated (inducible), depending on the promoter. Typically, transcription termination and polyadenylation sequences will also be present, located 3' to the translation stop codon. Examples of transcription terminator/polyadenylation signals include those derived from SV40 (Sambrook et al., supra). Introns, containing splice donor and acceptor sites, may also be designed into the constructs of the present invention.

Enhancer elements can also be used in the mammalian constructs to increase expression levels. Examples include the SV40 early gene enhancer (Dijkema et al., *EMBO J.* (1985) 4:761) and the enhancer/promoters derived from the long terminal repeat (LTR) of the Rous Sarcoma Virus (Gorman et al., *Proc. Natl. Acad. Sci. USA* (1982b) 79:6777) and human cytomegalovirus (Boshart et al., *Cell* (1985) 41:521). A leader sequence can also be present which includes a sequence encoding a signal peptide, to provide for the secretion of the foreign protein in mammalian cells. Preferably, there are processing sites encoded between the leader fragment and the gene of interest such that the leader sequence can be cleaved either in vivo or in vitro. The adenovirus tripartite leader is an example of a leader sequence that provides for secretion of a foreign protein in mammalian cells.

Once complete, the mammalian expression vectors can be used to transform any of several mammalian cells. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are also known and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), as well as others.

The constructs of the present invention can also be expressed in yeast. Control sequences for yeast vectors are known in the art and include promoters such as alcohol dehydrogenase (ADH) (EP Publication No. 284,044)., enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EP Publication No. 329,203). The yeast PHO5 gene, encoding acid phosphatase, also provides useful promoter sequences (Myanohara et al., *Proc. Natl. Acad. Sci. USA* (1983) 80:1). In addition, synthetic promoters which do not occur in nature also function as yeast promoters. For example, upstream activating sequences (UAS) of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EP Publication No. 164,556). Furthermore, a yeast promoter can include naturally occurring promoters of non-yeast origin that have the ability to bind yeast RNA polymerase and initiate transcription.

Other control elements which may be included in the yeast expression vectors are terminators (e.g., from GAPDH and from the enolase gene (Holland, *J. Biol. Chem.* (1981) 256:1385), and leader sequences which encode signal sequences for secretion. DNA encoding suitable signal sequences can be derived from genes for secreted yeast proteins, such as the yeast invertase gene (EP Publication No. 012,873; JPO Publication No. 62,096,086) and the α-factor gene (U.S. Pat. Nos. 4,588,684, 4,546,083 and 4,870,008; EP Publication No. 324,274; PCT Publication No. WO 89/02463). Alternatively, leaders of non-yeast origin, such as an interferon leader, also provide for secretion in yeast (EP Publication No. 060,057).

Expression and transformation vectors, either extrachromosomal replicons or integrating vectors, have been developed for transformation into many yeasts. For example, expression vectors have been developed for, inter alia, the following yeasts: *Saccharomyces cerevisiae* (Hinnen et al., *Proc. Natl. Acad. Sci. USA* (1978) 75:1929; Ito et al., *J. Bacteriol.* (1983) 153:163); *Saccharomyces carlsbergeneis*; *Candida albicans* (Kurtz et al., *Mol. Cell. Biol.* (1986) 6:142); *Candida maltosa* (Kunze et al., *J. Basic Microbiol.* (1985) 25:141); *Hansenula polymorpha* (Gleeson et al., *J. Gen. Microbiol.* (1986) 132:3459; Roggenkamp et al., *Mol. Gen. Genet.* (1986) 202:302); *Kluyveromyces fragilis* (Das et al., *J. Bacteriol.* (1984) 158:1165); *Kluyveromyces lactis* (De Louvencourt et al., *J. Bacteriol.* (1983) 154:737; Van den Berg et al., *Bio/Technology* (1990) 8:135); *Pichia guillerimondii* (Kunze et al.,*J. Basic Microbiol.* (1985) 25:141); *Pichia pastoris* (Cregg et al., *Mol. Cell. Biol.* (1985) 5:3376; U.S. Pat. Nos. 4,837,148 and 4,929,555); *Schizosaccharomyces pombe* (Beach and Nurse, *Nature* (1981) 300:706); and *Yarrowia lipolytica* (Davidow et al., *Curr. Genet.* (1985) 10:380471; Gaillardin et al., *Curr. Genet.* (1985) 10:49).

Methods of introducing exogenous DNA into yeast hosts are well known in the art, and typically include either the transformation of spheroplasts or of intact yeast cells treated with alkali cations.

Bacterial expression systems can also be used with the present constructs. Control elements for use in bacteria include promoters, optionally containing operator sequences, and ribosome binding sites. Useful promoters include sequences derived from sugar metabolizing enzymes, such as galactose, lactose (lac) and maltose. Additional examples include promoter sequences derived from biosynthetic enzymes such as tryptophan (trp), the b-lactamase (bla) promoter system, bacteriophage lambda PL, and T5. In addition, synthetic promoters, such as the tac promoter (U.S. Pat. No. 4,551,433), which do not occur in nature also function as in bacterial host cells.

The foregoing systems are particularly compatible with *E. coli*. However, numerous other systems for use in bacterial hosts such as *Bacillus* spp., *Streptococcus* spp., and *Streptomyces* spp., among others, are also known. Methods for introducing exogenous DNA into these hosts typically include the use of $CaCl_2$ or other agents, such as divalent cations and DMSO. DNA can also be introduced into bacterial cells by electroporation.

Other systems for expression of the desired antigens include insect cells and vectors suitable for use in these cells. The systems most commonly used are derived from the baculovirus *Autographa californica* polyhedrosis virus (AcNPV). Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene into the baculovirus genome); and appropriate insect host cells and growth media.

Promoters for use in the vectors are typically derived from structural genes, abundantly transcribed at late times in a viral infection cycle. Examples include sequences derived from the gene encoding the viral polyhedron protein, Friesen et al., (1986) "The Regulation of Baculovirus Gene Expression" in: *The Molecular Biology of Baculoviruses* (ed. Walter Doerfler); EP Publication Nos. 127,839 and 155,476; and the gene encoding the p10 protein Vlak et al., *J. Gen. Virol.* (1988) 69:765. The plasmid usually also contains the polyhedrin polyadenylation signal (Miller et al., *Ann. Rev. Microbiol.* (1988) 42:177) and a procaryotic ampicillin-resistance (amp) gene and origin of replication for selection and propagation in *E. coli*. DNA encoding suitable signal sequences can also be included and is generally derived from genes for secreted insect or baculovirus proteins, such as the baculovirus polyhedrin gene (Carbonell et al., *Gene* (1988) 73:409), as well as mammalian signal sequences such as those derived from genes encoding human α-interferon, Maeda et al., *Nature* (1985) 315:592; human gastrin-releasing peptide, Lebacq-Verheyden et al., *Molec. Cell. Biol.* (1988) 8:3129; human IL-2, Smith et al., *Proc. Natl. Acad. Sci. USA* (1985) 82:8404; mouse IL-3, (Miyajima et al., *Gene* (1987) 58:273; and human glucocerebrosidase, Martin et al., *DNA* (1988) 7:99.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 bps downstream from the ATT; see Luckow and Summers, *Virology* (1989) 17:31).

The desired DNA sequence is inserted into the transfer vector, using known techniques (see, Summers and Smith, supra; Smith et al., *Mol. Cell. Biol.* (1983) 3:2156; and Luckow and Summers (1989) and an insect cell host is cotransformed with the heterologous DNA of the transfer vector and the genomic DNA of wild type baculovirus—usually by cotransfection. The vector and viral genome are allowed to recombine. The packaged recombinant virus is expressed and recombinant plaques are identified and purified. Materials and methods for baculovirus/insect cell expression systems are commercially available in kit form from, for example, Invitrogen, San Diego Calif. ("MaxBac" kit). These techniques are generally known to those skilled in the art and fully described in Summers and Smith, *Texas Agricultural Experiment Station Bulletin No.* 1555 (1987) (hereinafter "Summers and Smith").

Recombinant baculovirus expression vectors have been developed for infection into several insect cells. For example, recombinant baculoviruses have been developed for, inter alia: *Aedes aegypti*, *Autographa californica*, *Bombyx mori*, *Drosophila melanogaster*, *Spodoptera frugiperda*, and *Trichoplusia ni*.

It is often desirable that the polypeptides prepared using the above systems be fusion polypeptides. As with nonfusion proteins, these proteins may be expressed intracellularly or may be secreted from the cell into the growth medium.

Furthermore, plasmids can be constructed which include a chimeric gene sequence, encoding e.g., multiple type-specific *H. pylori* Type I antigens or multiple type-common antigens. The gene sequences can be present in a dicistronic gene configuration. Additional control elements can be situated between the various genes for efficient translation of RNA from the distal coding region. Alternatively, a chimeric transcription unit having a single open reading frame encoding the multiple antigens can also be constructed. Either a fusion can be made to allow for the synthesis of a chimeric protein or alternatively, protein processing signals can be engineered to provide cleavage by a protease, thus allowing liberation of the two or more proteins derived from translation of the template RNA. The processing protease may also be expressed in this system either independently or as part of a chimera with the antigen coding region(s).

Viral systems, such as a vaccinia based infection/transfection system, as described in Tomei et al., *J. Virol.* (1993) 67:4017–4026 and Selby et al., *J. Gen. Virol.* (1993) 74:1103–1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

Depending on the expression system and host selected, the antigens of the present invention are produced by growing host cells transformed by an expression vector under conditions whereby the antigen of interest is expressed. The antigen is then isolated from the host cells and purified. If the expression system provides for secretion of the antigen, the antigen can be purified directly from the media. If the antigen is not secreted, it is isolated from cell lysates. The selection of the appropriate growth conditions and recovery methods are within the skill of the art.

The *H. pylori* antigens may also be produced by chemical synthesis such as by solid phase or solution peptide synthesis, using methods known to those skilled in the art. Chemical synthesis of peptides may be preferable if the antigen in question is relatively small. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis.

The *H. pylori* type-common and type-specific *H. pylori* Type I antigens are used herein as diagnostics to detect the presence of reactive antibodies directed against the bacterium in a biological sample. Furthermore, the antigens can be used to monitor the course of antibiotic therapy by comparing results obtained at the outset of therapy to those obtained during and after a course of treatment. For example, the presence of antibodies reactive with the type-common and/or the type-specific *H. pylori* antigens can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more type-common and/or one or more type-specific *H. pylori* Type I antigens) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A., *Bioconjugate Chem.* (1992) 3:2–13; Hashida et al., *J. Appl. Biochem.* (1984) 6:56–63; and Anjaneyulu and Staros, *International J. of Peptide and Protein Res.* (1987) 30:117–124.

After reacting the solid support with the solid phase component, any non-immobilized solid-phase components are removed from the support by washing, and the support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, where the secondary binder is capable of associating selectively with the bound ligand. The presence of the secondary binder can then be detected using techniques well known in the art.

More particularly, an ELISA method can be used, where the wells of a microtiter plate are coated with the *H. pylori* type-common and/or the type-specific *H. pylori* Type I antigen(s). A biological sample containing or suspected of containing anti-*H. pylori* immunoglobulin molecules is then added to the coated wells. In assays where it is desired to use one microtiter plate, a selected number of wells can be coated with, e.g., a first type-specific antigen moiety, a different set of wells coated with a second type-specific antigen moiety and a third set of wells with the *H. pylori* type-common antigen, etc. In the alternative, a series of ELISAs can be run in tandem, wherein individual plates are used for each type-common and type-specific antigen moiety. After a period of incubation sufficient to allow antibody binding to the immobilized antigens, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-type-specific and/or anti-*H. pylori* type-common antigen ligands from a biological sample can be readily detected using a secondary binder comprising an antibody directed against the antibody ligands. A number of anti-human immunoglobulin (Ig) molecules are known in the art (e.g., commercially available goat anti-human Ig or rabbit anti-human Ig). Ig molecules for use herein will preferably be of the IgG or IgA type, however, IgM may also be appropriate in some instances. The Ig molecules can be readily conjugated to a detectable enzyme label, such as horseradish peroxidase, glucose oxidase, Beta-galactosidase, alkaline phosphatase and urease, among others, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the bacterial proteins and antibodies specific for those bacterial proteins form complexes under precipitating conditions. In one particular embodiment, the *H. pylori* type-common and/or the type-specific antigen(s) can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for *H. pylori* Type I or Type II. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing anti-*H. pylori* antibodies is immobilized to a substrate. In this regard, an initial affinity purification of the sample can be carried out using immobilized antigens. The resultant sample preparation will thus only contain anti-*H. pylori* moieties, avoiding potential nonspecific binding properties in the affinity support. A number of methods of immobilizing immunoglobulins (either intact or in specific fragments) at high yield and having good retention of antigen binding activity, are known in the art. Not being limited by any particular method, immobilized protein A or protein G can be used to immobilize immunoglobulins.

Accordingly, once the immunoglobulin molecules have been immobilized to provide an immunoaffinity matrix, the *H. pylori* type-common and type-specific antigens, having separate and distinct labels, are contacted with the bound antibodies under suitable binding conditions. After any non-specifically bound antigen has been washed from the immunoaffinity support, the presence of bound antigen can be determined by assaying for each specific label using methods known in the art.

A particularly preferred method for diagnosing *H. pylori* infection and monitoring the course of treatment using the present invention involves the use of strip immunoblot assay (SIA) techniques, such as those known in the art which combine traditional Western and dot blotting techniques, e.g., the RIBA® (Chiron Corp., Emeryville, Calif.) test. In these assays, the *H. pylori* type-common and type-specific *H. pylori* Type I antigens are immobilized as individual, discrete portions, e.g., as bands or dots, on a membranous support. Thus, by "discretely immobilized" on a membrane support is meant that the antigens are present as separate components and are not mixed, such that reactivity or lack thereof with each of the antigens present can be assessed. A biological sample suspected of containing antibodies to *H. pylori* antigens is then reacted with the test membrane. Visualization of anti-*H. pylori* reactivity in the biological sample is accomplished using anti-human IgG enzyme-conjugates in conjunction with a colorimetric enzyme substrate. Internal controls, such as human IgM and human IgG, can also be present on the strip. The assay can be performed manually or used in an automated format.

Generally, the type-specific antigens, such as VacA and CagA, are applied to the strip in a concentration of about 0.5 to about 5 μg/ml, more preferably about 0.5 to 3 μg/ml and most preferably about 1–2 μg/ml. Alternatively, two concentrations of antigen can be present, such as a low concentration and a high concentration, to provide a strip that can be used both for diagnosis of infection, as well as to monitor the response to treatment. Thus, for example, VacA and/or CagA can be provided in a concentration as specified above, as well as in one or more additional bands, in a concentration of about 0.005–0.4 μg/ml, more preferably about 0.008–3 μg/ml and most preferably about 0.1–0.2 μg/ml. The type-common antigen, e.g., the *H. pylori* lysate, can be applied at a concentration of about 0.25–2 μg/ml, more preferably about 0.25–1.5 μg/ml and most preferably about 0.5–1 μg/ml. It is readily apparent that the concentration of antigen to be applied to the test strip will vary depending on the specific antigen used and can be readily determined by one of skill in the art.

The Ig controls, such as IgG, can be present in a single concentration, or in two concentrations, one low and one high. For example, IgG can be present in a concentration of about 50–250 ng/ml, more preferably about 75–200 ng/ml and most preferably about 100–185 ng/ml. A higher concentration of IgG can also be present along with the low concentration of IgG, to provide another internal control, such as at a concentration of about 400–1200 ng/ml, more preferably about 450–1000 ng/ml and most preferably about 500–950 ng/ml.

The above-described assay reagents, including the *H. pylori* lysate and type-specific antigens, optionally immobilized on a solid support, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Production of an *H. pylori* VacA Polypeptide

A VacA polypeptide was produced recombinantly as a fusion protein of 71.2 kDa which included 154 amino acids of human superoxide dismutase (SOD) (Hallewell et al., *Nucl. Acids Res.* (1985) 13:2017–2134), a linker of five amino acids (Asn-Leu-Gly-Ile-Leu) and the VacA amino acid sequence Gly-311 through Ile-819 of *H. pylori* CCUG17874 (Covacci et al., *Proc. Natl. Acad. Sci. USA* (1993) 90:5791–5795; Telford et al., *J. Exp. Med.* (1994) 179:1653–1658).

In particular, DNA encoding for the truncated VacA protein was synthesized by PCR and fused in frame with DNA sequences coding for SOD. The glucose regulated ADH2/GAPDH promoter (Cousens et al., *Gene* (1984) 61:265–275) was then incorporated at the 5'-end of the amplified fragment and the resulting cassette was cloned into the yeast expression vector pBS24.1 (Pichuantes et al., *Protein Eng., Principle and Prac.* (1996) 5:129–161). This vector contains $2\mu$ and inverted repeat (IR) sequences for autonomous replication in yeast, the α-factor terminator to ensure transcription termination, the leu2-d and URA3 yeast genes for selection, and the β-lactamase gene and the ColE1 origin of replication for selection and propagation in *E. coli*. High expression levels of the *H. pylori* VacA recombinant protein were obtained in *Saccharomyces cerevisiae* JSC310 (Mat a, leu2, ura3-52, prbl-1122, pep4-3, prcl-407,::pDM15 (G418$^R$), [cir$^0$]) as evidenced by Coomassie-blue staining and immunoblot analysis of yeast proteins separated by SDS-PAGE. The nucleotide and corresponding amino acid sequence of the VacA recombinant protein is shown in FIGS. 3A–3B (SEQ ID NOS: 1 and 2).

The VacA recombinant protein was purified from yeast cells harvested several hours after depletion of glucose from the medium. This condition is needed to activate the ADH2/GAPDH promoter and trigger production of the foreign protein (Pichuantes et al., *J. Biol. Chem.* (1990) 265:13890–13898). Cells were broken with glass beads in a Dynomill using a lysis buffer containing 50 mM Tris-HCl (pH 8.0), 150 mM NaCl, 1 mM EDTA, 1 mM PMSF. The protein was recovered from the insoluble fraction (obtained by centrifugation at 48,400×g for 30 minutes) with increasing amounts of urea (1M to 3M) in lysis buffer. After centrifugation at 48,400×g for 30 minutes, the pellet containing the protein of interest was solubilized with lysis buffer containing 4M urea, 50 mM DTT, 1N NaOH, while stirring on ice for 30 minutes. After removal of cell debris by centrifugation, the suspension was immediately titrated back to pH 8.0 with 6N NaOH. The supernatant was made 2.3% SDS, boiled for 3 minutes, cooled to room temperature and loaded onto a Sephacryl S-400 gel filtration column (Pharmacia) using a buffer containing PBS, 0.1 mM EDTA, 0.1% SDS, pH 7.4. Fractions containing the recombinant VacA protein were pooled and concentrated in an Amicon concentrator (YM-10 membrane). After adjusting SDS to 2.3% and DTT to 50 mM, the suspension was loaded back onto the same S-400 column for further fractionation. This procedure yielded a VacA protein >90 pure.

EXAMPLE 2

Production of an *H. pylori* CagA Polypeptide

A CagA polypeptide of 268 amino acids and having a molecular weight of 29.2 kDa, including amino acids Glu-748 through Glu-1015 of the CagA protein of the Chilean strain of *Helicobacter pylori*, Chetx-1, was produced recombinantly as follows. The DNA coding for this truncated CagA protein was synthesized by PCR and the initiation codon ATG was introduced at the 5'-end of the amplified fragment. The ADH2/GAPDH hybrid promoter (Cousens et al., *Gene* (1984) 61:265–275) was then incorporated at the 5'-end of the PCR-synthesized fragment and the resulting cassette was cloned into the yeast expression vector pBS24.1, essentially as described above. The resulting recombinant plasmid was used to transform *Saccharomyces cerevisiae* AD3 (Mat a, leu2, ura3-52, prb1-1122, pep4-3, prcl-407, ::pDM15 (G418$^R$), LEU2(ΔAD), [CIR$^0$]) and expression of the recombinant antigen was monitored by Coomassie blue staining and immunoblot analysis of yeast proteins fractionated by SDS-PAGE. The nucleotide and corresponding amino acid sequence of the CagA recombinant protein is shown in FIG. 4.

The CagA recombinant protein was purified from yeast cells suspended in lysis buffer (50 mM Tris-HCl, 150 mM NaCl, 1 mM EDTA, 1 mM PMSF, pH 8.0) and disrupted with glass beads in a Dynomill. After centrifugation at 48,400×g for 30 minutes, the supernatant was made 4M urea, diluted 1/10 (v/v) with S Sepharose IEC equilibration buffer to OD$_{289}$=0.00 and the protein was eluted with a linear gradient of 0 to 0.5M NaCl in equilibration buffer. The elution peak containing the CagA protein was collected and precipitated with 30% ammonium sulfate. After centrifugation at 17,700×g for 30 minutes, the pellet was discarded and the supernatant was precipitated with a further 10% solid ammonium sulfate under the conditions described above. The pellet obtained after centrifugation at 17,700×g for 30 minutes was dissolved in a minimum amount of PBS/8M urea, adjusted to 2.3% SDS/50 mM DTT, boiled for 3 minutes, cooled to room temperature and loaded onto a Sephacryl S-300 gel filtration column (Pharmacia) using a buffer containing PBS, 0.1 mM SDS, 1 mM EDTA, pH 7.4. The fractions containing the protein of interest were collected and concentrated in an Amicon concentrator (YM-10 membrane). The concentrated material was made 2.3% SDS/50 mM DTT and loaded back onto the same S-300 column for a second fractionation. This procedure yielded a CagA protein >90% pure.

EXAMPLE 3

*H. pylori* Strip Immunoblot Assay (SIA) Using Type-Specific and Type-Common *H. pylori* Antigens A. An SIA was done as follows. An *H. pylori* extract containing a mixture of antigens including type-common antigens was obtained from Bioseed, Inc., Hillsborough, Calif. Briefly, the extract was prepared from an *H. pylori* bacterium obtained from the American Type Culture Collection (ATCC) having an ATCC strain designation of ATCC 43504. The extract was prepared using detergent extraction and sonication.

The VacA and CagA type-specific antigens, described in Examples 1 and 2, respectively, were applied in discrete bands to nitrocellulose strips at concentrations of 1–2 μg/ml. The lysate including the type-common antigens was coated as another discrete band at a concentration of 0.5–1 μg/ml onto the same nitrocellulose strips. As internal controls, additional bands contained purified human IgG at a low (100–185 ng/ml) and high (500–925 ng/ml) concentration. Other strips were coated with the antigens and lysate as described above, however, on these strips, the lysate was first enhanced with the VacA and CagA antigens added to the lysate at a concentration of 0.5–1 μg/ml (VacA) and 0.5-μg/ml (CagA). FIG. 1 is a diagram of a nitrocellulose strip with the antigens as described above.

For the immunoblot assay, strips were processed in a batch fashion with 30 strips per batch. All steps were performed at room temperature. Each strip was numbered and then placed in a separate tube to which was added 1 ml of diluent (phosphate-buffered saline (PBS) with bovine protein stabilizers and detergents, 0.1% sodium azide and 0.05% gentamicin sulfate as preservatives) and 30 μl of a serum sample from an individual known to be infected with *H. pylori* Type I, suspected of being infected with *H. pylori* Type I or a control subject, was applied. The tubes were rocked gently for 4 h, the solution removed by aspiration, and 1 ml of fresh diluent was added to each tube. The tubes were rocked for 30 minutes, the solution removed by aspiration and 1 ml of wash buffer made from wash buffer concentrate (50×) (phosphate-buffered detergent solution with 0.01% thimerosal as a preservative) was added to each tube. The contents of each tube were emptied into a single wash vessel and the strips were washed by swirling for 20 seconds. The wash buffer was decanted and 30 ml of fresh buffer added and the process repeated. Residual solution was removed by aspiration and 20 ml of conjugate solution (peroxidase-labeled goat anti-human IgG (heavy and light chains), with bovine protein stabilizers, containing 0.01% thimerosal as a preservative) was added. The vessel was rotated at 110 rpm for 10 minutes, the conjugate solution was decanted and the wash step was repeated three times. Residual solution was again removed by aspiration and 20 ml of substrate/developer (4-chloro-1-napthol in methanol/phosphate-buffered hydrogen peroxide) added, followed by rotation for 15–20 minutes at 110 rpm. The solution was decanted and the strips were washed twice in distilled water. Developed strips were placed face up on absorbent paper and allowed to dry for 30 minutes in the dark. Strips were then read within 3 h of drying. The intensity of the color of the *H. pylori* antigen bands were assigned values ranging from –(0) to 4+using the following algorithm. The low IgG band is assigned a value of 1+, the high IgG band is assigned a value of 3+. The lysate and VacA and CagA bands are then scored from 0 to 4+according to how their band intensity compares to that of the IgG control bands.

Samples with any of the *H. pylori* antigen bands scoring 1+ or greater to the lysate band are considered to be positive for *H. pylori* infection. Reactivity of 1+ or greater to the lysate band, in addition to reactivity of 1+ or greater to the CagA and/or VacA band, is considered positive for *H. pylori* Type I infection. Samples showing no reactivity of 1+ or greater to any bands are considered negative.

Using this assay, 29 samples obtained from individuals determined to be positive for *H. pylori* infection by endoscopy, 12 with duodenal ulcers, 9 with gastric ulcers and 8 with gastritis, were tested for reactivity. In another study, 80 individuals known to have duodenal ulcers were tested. The results are shown in Tables 1 and 2, respectively. As can be seen, the assay is highly predictive of *H. pylori* infection.

TABLE 1

Frequency of Band Reactivity
(*H. Pylori* Endoscopy Positive Specimens n = 29)

|  | Lysate | Lysate + CagA | Lysate + CagA and/or VacA | CagA and/or VacA |
|---|---|---|---|---|
| D. Ulcer (n = 12) | 11/12 91.7% | 10/12 83.3% | 10/12 83.3% | 1/12 8.3% |
| G. Ulcer (n = 9) | 9/9 100% | 7/9 77.8% | 8/9 88.9% | 0/9 0.0% |
| Gastritis (n = 8) | 6/8 75.0% | 4/8 50.0% | 4/8 50.0% | 1/8 12.5% |

TABLE 2

Frequency of Band Reactivity in a Duodenal Ulcer Population

| Lysate | Lysate + CagA | Lysate + CagA and/or VacA | CagA and/or VacA |
|---|---|---|---|
| 78/80 (97.5%) | 71/80 (88.8%) | 75/80 (93.8%) | 2/80 (2.5%) |

The above assay was also used to test samples from individuals undergoing antibiotic therapy for *H. pylori* infection. Table 3 shows a comparison between a person responding positively to antibiotic therapy (responder) and one not responding to therapy (non-responder). Samples from the responder were taken at 1, 3, 6, 9 and 12 months and samples from the non-responder taken at 8 and 16 months. As shown in Table 3, reactivity with the antigens decreased with time with the responder but did not significantly change with the non-responder.

TABLE 3

Therapy Monitoring of *H. pylori* Infections

|  | Lysate | CagA | VacA |
|---|---|---|---|
| I. Responder |  |  |  |
| Prebleed | 3.42 | 1.92 | 0.31 |
| 1 M | 2.87 | 1.69 | 0.26 |
| 3 M | 2.32 | 1.09 | 0.33 |
| 6 M | 2.25 | 0.90 | 0.29 |
| 9 M | 2.13 | 0.73 | 0.21 |
| 12 M | 1.32 | 0.43 | 0.18 |
| II. Non-Responder |  |  |  |
| Prebleed | 3.38 | 1.31 | 2.54 |
| 8 M | 3.06 | 0.99 | 2.49 |
| 16 M | 2.92 | 0.90 | 2.10 |

In another study, samples were obtained from individuals undergoing three different types of antibiotic regimens, as shown in Table 4. As can be seen, the response rate reported correlated with the results using the assay above for those individuals undergoing the triple and single antibiotic regimens.

TABLE 4

Therapy Monitoring of *H. pylori* Infection

| Therapy Regimen | Response Rate Reported | % Responders |
|---|---|---|
| Triple | 73% | 15/20 (75%) |
| Double | 48% | 11/17 (65%) |
| Single | 19% | 1/5 (20%) |

Triple = Metronidazole + Bismuth + Amoxicillin
Double = Metronidazole + Bismuth
Single = Metronidazole These two studies show that the assay is useful for determining whether an individual is responding to treatment.

Figure 2:
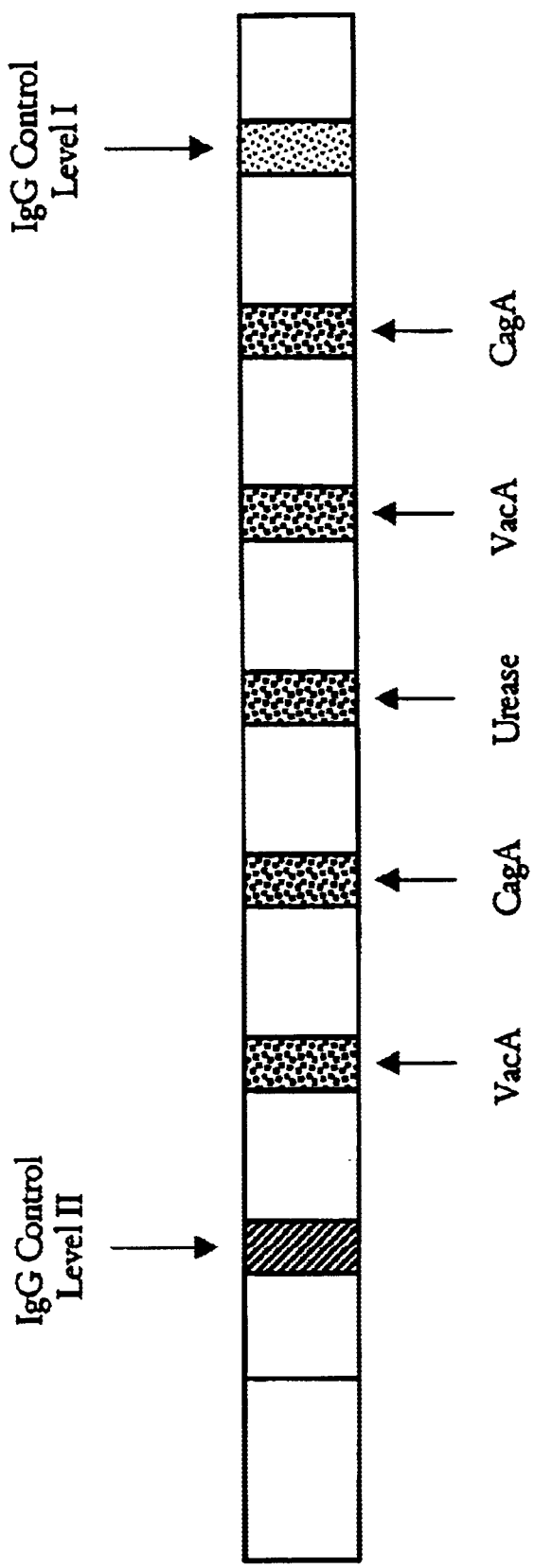
FIG. 2 shows another representative test strip for use in an SIA. As above, human IgG is used as an internal control at two different levels (Level I, low control; and Level II, high control). CagA and VacA are used as the type-specific *H. pylori* Type I antigens and are also used at two different levels to enhance the sensitivity of the assay as well as to monitor response to treatment. Urease is used as the type-common antigen.

B. Another SIA was done as follows. *H. pylori* urease was applied as a narrow band to nitrocellulose strips at a concentration of 1–2 μg/ml. The VacA antigen, described above, was applied at two concentrations, 1–2 μg/ml and 0.1–0.2 μg/ml, to the same strips. The CagA type-specific antigen was also applied to the strips at the same two concentrations. As internal controls, additional bands contained purified human IgG at a low (100–185 ng/ml) and high (500–925 ng/ml) concentration. FIG. 2 is a diagram of a nitrocellulose strip with the antigens as described above.

The assay was performed as described above. The intensity of the color of the *H. pylori* antigen bands were assigned values, also as described above.

Thus, novel methods for detecting *H. pylori* infection as well as distinguishing between *H. pylori* Type I and Type II, and for monitoring the course of treatment, are disclosed. Although preferred embodiments of the subject invention have been described in some detail, it is understood that obvious variations can be made without departing from the spirit and the scope of the invention as defined by the appended claims.

---

What is claimed is:

1. A method of detecting *Helicobacter pylori* antibodies associated with infection in a human subject comprising:

(a) reacting a biological sample from the subject with one or more *H. pylori* type-common antigens provided in an *H. pylori* lysate and with one or more purified type-specific *H. pylori* Type I antigens, wherein the type-specific antigens are *H. pylori* vacuolating cytotoxin (VacA) and cytotoxin associated antigen (CagA), under conditions which allow *H. pylori* antibodies, when present in the biological sample, to specifically bind with said type-common antigens or said type-specific antigen(s);

(b) removing unbound antibodies;

(c) providing one or more moieties comprising a detectably labeled anti-human immunoglobulin antibody which bind to said bound antibodies;

(d) detecting the presence or absence of said one or more moieties;

(e) correlating the presence of antibodies that specifically bind to the type-specific antigens to infection with Type I *H. pylori*; and (f) correlating the absence of antibodies that specifically bind to the type-specific antigens and the presence of antibodies that specifically bind to the type-common antigens to infection with Type II *H. pylori*.

2. The method of claim 1, wherein said *H. pylori* infection is *H. pylori* Type I.

3. The method of claim 1, wherein said *H. pylori* infection is *H. pylori* Type II.

4. The method of claim 1, wherein the detectable label is a fluorescer or an enzyme.

5. The method of claim 1, wherein said one or more type-common antigens and said one or more type-specific antigens are immobilized on a solid support or are immobilized on different solid supports.

6. The method of claim 5 wherein said one or more type-common antigens and said one or more type-specific antigens are immobilized on the same solid support.

7. The method of claim 5 wherein said one or more type-common antigens and said one or more type-specific antigens are immobilized on different solid supports.

8. The method of claim 5 wherein the solid support is a nitrocellulose strip.

9. The method of claim 1, wherein said one or more type-common antigens comprises an *H. pylori* urease.

10. The method of claim 1, wherein said biological sample is a serum sample.

11. A method for distinguishing between *Helicobacter pylori* Type I and *Helicobacter pylori* Type II antibodies associated with infection in a human serum sample, said method comprising:

(a) immobilizing an *H. pylori* lysate comprising one or more *H. pylori* type-common antigens and one or more purified type-specific *H. pylori* Type I antigens on at least one nitrocellulose strip, wherein the type-specific antigens are *H. pylori* vacuolating cytotoxin (VacA) and cytotoxin associated antigen (CagA);

(b) contacting said nitrocellulose strip from step (a) with said human serum sample under conditions which allow anti-*H. pylori* Type I and anti-*H. pylori* Type II antibodies, when present in the sample, to specifically bind with *H. pylori* type-common and type-specific *H. pylori* Type I antigens present in said lysate;

(c) removing unbound antibodies;

(d) providing a detectably labeled anti-human immunoglobulin antibody;

(e) detecting the presence or absence of bound anti-human immunoglobulin antibodies to said at least one nitrocellulose strip;

(f) correlating the presence of antibodies that specifically bind to the type-specific antigens to infection with Type I *H. pylori*; and (g) correlating the absence of antibodies that specifically bind to the type-specific antigens and the presence of antibodies that specifically bind to the type-common antigens to infection with Type II *H. pylori*.

12. The method of claim 11 wherein said one or more type-common antigens and said one or more type-specific antigens are immobilized on the same nitrocellulose strip.

13. The method of claim 11, wherein said one or more type-common antigens and said one or more type-specific antigens are immobilized on different nitrocellulose strips.

14. A method of monitoring a human subject undergoing therapy for an *Helicobacter pylori* infection comprising:

(a) providing a biological sample from the human subject;

(b) immobilizing an *H. pylori* lysate comprising one or more *H. pylori* type-common antigens and one or more purified type-specific *H. pylori* Type I antigens on at least one nitrocellulose strip, wherein the type-specific antigens are *H. pylori* vacuolating cytotoxin (VacA) and cytotoxin associated antigen (CagA);

(c) contacting said nitrocellulose strip from step (b) with said biological sample under conditions which allow anti-*H. pylori* Type I and anti-*H. pylori* Type II antibodies, when present in the biological sample, to specifically bind with *H. pylori* type-common and type-specific *H. pylori* Type I antigens present in said lysate;

(d) removing unbound antibodies;

(e) providing a detectably labeled anti-human immunoglobulin antibody;

(f) detecting the presence or absence of bound anti-human immunoglobulin antibodies in said biological sample;

(g) correlating the presence of antibodies that specifically bind to the type-specific antigens to infection with Type I *H. pylori*; and (h) correlating the absence of antibodies that specifically bind to the type-specific antigens and the presence of antibodies that specifically bind to the type-common antigens to infection with Type II *H. pylori*, thereby monitoring the course of treatment of the infection.

15. The method of claim 14 wherein said one or more type-common antigens and said one or more type-specific antigens are immobilized on the same nitrocellulose strip.

16. The method of claim 14, wherein said one or more type-common antigens and said one or more type-specific antigens are immobilized on different nitrocellulose strips.

17. The method of claim 14, wherein said biological sample is a serum sample.

* * * * *